(12) United States Patent
Thiele et al.

(10) Patent No.: US 9,156,775 B2
(45) Date of Patent: Oct. 13, 2015

(54) SUBSTITUTED 1,3-THIAZOLES AS HEAT SHOCK TRANSCRIPTION FACTOR 1 ACTIVATORS

(75) Inventors: Dennis J. Thiele, Chapel Hill, NC (US); Daniel W. Neef, Durham, NC (US); Jose S. Mendoza, Chapel Hill, NC (US)

(73) Assignees: DUKE UNIVERSITY, Durham, NC (US); CHAPERONE THERAPEUTICS, INC., Durham, NC (US)

( * ) Notice: Subject to any disclaimer, the term of this patent is extended or adjusted under 35 U.S.C. 154(b) by 0 days.

(21) Appl. No.: 13/884,666

(22) PCT Filed: Nov. 8, 2011

(86) PCT No.: PCT/US2011/059741
§ 371 (c)(1),
(2), (4) Date: May 30, 2013

(87) PCT Pub. No.: WO2012/064715
PCT Pub. Date: May 18, 2012

(65) Prior Publication Data
US 2013/0267543 A1      Oct. 10, 2013

Related U.S. Application Data

(63) Continuation of application No. 12/945,522, filed on Nov. 12, 2010.

(51) Int. Cl.
| | | |
|---|---|---|
| C07D 277/38 | (2006.01) | |
| C07C 211/01 | (2006.01) | |
| A61K 31/415 | (2006.01) | |
| A61K 31/4155 | (2006.01) | |
| A61K 31/426 | (2006.01) | |
| A61K 45/06 | (2006.01) | |
| C07D 231/40 | (2006.01) | |
| C07D 277/42 | (2006.01) | |
| C07D 277/60 | (2006.01) | |
| C07D 409/04 | (2006.01) | |
| C07K 14/47 | (2006.01) | |
| C07D 231/38 | (2006.01) | |
| C07D 405/14 | (2006.01) | |
| C07D 413/12 | (2006.01) | |

(52) U.S. Cl.
CPC ............ *C07C 211/01* (2013.01); *A61K 31/415* (2013.01); *A61K 31/4155* (2013.01); *A61K 31/426* (2013.01); *A61K 45/06* (2013.01); *C07D 231/38* (2013.01); *C07D 231/40* (2013.01); *C07D 277/38* (2013.01); *C07D 277/42* (2013.01); *C07D 277/60* (2013.01); *C07D 405/14* (2013.01); *C07D 409/04* (2013.01); *C07D 413/12* (2013.01); *C07K 14/47* (2013.01)

(58) Field of Classification Search
CPC .................................................. C07D 277/38
USPC .............. 544/369; 546/304; 548/190; 549/68
See application file for complete search history.

(56) References Cited

U.S. PATENT DOCUMENTS

| | | | | |
|---|---|---|---|---|
| 6,586,453 | B2 * | 7/2003 | Dhanoa et al. ................. | 514/365 |
| 7,781,442 | B2 * | 8/2010 | Cheng et al. .................. | 514/269 |
| 2005/0192294 | A1 | 9/2005 | Rudolph | |

FOREIGN PATENT DOCUMENTS

| | | |
|---|---|---|
| JP | 2007/525513 | 12/2006 |
| WO | 01/32648 | 5/2001 |
| WO | 2004/016592 | 2/2004 |
| WO | 2004/043951 | 5/2004 |
| WO | 2004/110350 | 12/2004 |
| WO | 2005/000300 | 1/2005 |
| WO | 2005/026137 | 3/2005 |
| WO | 2005/041879 | 5/2005 |
| WO | 2005/044194 | 5/2005 |
| WO | 2005/086656 | 9/2005 |
| WO | 2006/013054 | 2/2006 |
| WO | 2007/120343 | 10/2007 |
| WO | 2009/140621 | 11/2009 |

OTHER PUBLICATIONS

Jordan, V.C., Tamoxifen: A Most Unlikely Pioneering Medicine. Nature Reviews: Drug Discovery, 2 (2003) 205-211.
Zaragoza, Dorwald F., Side Reactions in Organic Synthesis: A Guide to Successful Synthesis Design, Weinheim: Wiley-VCH Verlag GmbH & Co. KGaA (2005) Preface.
Vippagunta, et al., Crystalline solids. Advanced Drug Delivery Reviews, 48 (2001) pp. 3-26.
Lu, et al., Structure-Based Drug Design of a Novel Family of PPARγ Partial Agonists: Virtual Screening, X-ray Crystallography, and in Vitro/in Vivo Biological Activities. Journal of Medicinal Chemistry, 49(9) (2006) 2703-2712.
Wolff, Manfred E., Ed. Burger's Medicinal Chemistry and Drug Discovery—Fifth Edition, New York: John Wiley & Sons (1996) 1, 975-977.
Borghini A., et al., "QSAR study on thiazole and thiadiazole analogues as antagonists for the adenosine A1 and A3 receptors," Bioorganic & Medicinal Chemistry, Pergamon, GB, vol. 13, No. 18, Sep. 15, 2005, pp. 5330-5337.
Gablyos A., et al., "Synthesis and biological evaluation of 2-aminothiazoles and their amide derivatives on human adenosine receptors. Lack of effect of 2-aminothiazoles as allosteric enhancers," Bioorganic & Medicinal Chemistry, Pergamon, GB, vol. 13, No. 6, Mar. 15, 2005, pp. 2079-2087.

(Continued)

*Primary Examiner* — Douglas M Willis
(74) *Attorney, Agent, or Firm* — Casimir Jones, S.C.

(57) ABSTRACT

The present invention relates to 1,3-thiazole compounds, methods for their discovery, and their research and therapeutic uses, as well as pharmaceutically acceptable salts, solvates, chelates, non-covalent complexes, prodrugs, mixtures (including both R and S enantiomeric forms and racemic mixtures thereof), and pharmaceutical Formulations thereof.

1 Claim, 4 Drawing Sheets

(56) References Cited

OTHER PUBLICATIONS

JP Office Action (and English Translation) from related JP Patent Application No. 2013-538824, mailed Jul. 15, 2014.
Adachi et al., 2003, "Heat shock protein 70 chaperone overexpression ameliorates phenotypes of the spinal and bulbar muscular atrophy transgenic mouse model by reducing nuclear-localized mutant androgen receptor protein", J. Neurosci, 23: 2203-2211.
Ali et al., 1998, "HSP90 interacts with and regulates the activity of heat shock factor 1 in Xenopus oocytes", Mol. Cell. Biol., 18: 4949-4960.
Amolins et al., 2009, "Natural product inhibitors of Hsp90: potential leads for drug discovery", Mini Rev. Med. Chem., 9: 140-152.
Bagley et al., 2006, "Microwave-assisted synthesis of N-pyrazole ureas and the p38alpha inhibitor BIRB 796 for study into accelerated cell ageing", Org. Biomol. Chem, 4: 4158-4164.
Bailey et al., 2002, "Molecular chaperones enhance the degradation of expanded polyglutamine repeat androgen receptor in a cellular model of spinal and bulbar muscular atrophy", Hum. Mol. Genet., 11(5): 515-523.
Bonini, 2002, "Chaperoning brain degeneration", Proc. Natl. Acad. Sci., 99: 16407-16411.
Bukau et al., 2000, "Getting newly synthesized proteins into shape", Cell, 101(2):119-122.
Bukau et al., 2006, "Molecular chaperones and protein quality control", Cell, 125(3): 443-451.
Chai et al., 1999, "Analysis of the role of heat shock protein (Hsp) molecular chaperones in polyglutamine disease", J. Neurosci, 19(23): 10338-10347.
Cummings et al., 2000, "Fourteen and counting: unraveling trinucleotide repeat diseases", Hum. Mol. Genet., 9: 909-916.
Cummings et al., 2001, "Over-expression of inducible HSP70 chaperone suppresses neuropathology and improves motor function in SCA1 mice", Hum. Mol. Genet, 10: 1511-1518.
Deuerling et al., 2004, "Chaperone-assisted folding of newly synthesized proteins in the cytosol", Crit. Rev. Biochem. Mol. Biol., 39: 261-277.
Dickey et al., 2007, "Brain CHIP: Removing the culprits in neurodegenerative disease", Trends Mol. Med, 13(1): 32-38.
Finkbeiner et al., 2006, "Disease-modifying pathways in neurodegeneration", J. Neurosci, 26(41): 10349-10357.
Furukawa et al., 2006, "Disulfide cross-linked protein represents a significant fraction of ALS-associated Cu, Zn-superoxide dismutase aggregates in spinal cords of model mice", PNAS, 103(18): 7148-7153.
Gidalevitz et al., 2006, "Progressive disruption of cellular protein folding in models of polyglutamine diseases", Science, 311: 1471-1474.
Guo et al., 2001, "Evidence for a mechanism of repression of heat shock factor 1 transcriptional activity by a multichaperone complex", J. Biol. Chem, 276(49):45791-9.
Hahn et al., 2004, "Genome-wide analysis of the biology of stress responses through heat shock transcription factor", Molecular and Cellular Biology, 24: 5249-5256.
Hartl, 1996, "Molecular chaperones in cellular protein folding", Nature, 381: 571-580.
Hsu, 2003, "Regulation of aging and age-related disease by DAF-16 and heat-shock factor", Science, 300: 1142-1145.
Jana et al., 2000, "Polyglutamine length-dependent interaction of Hsp40 and Hsp70 family chaperones with truncated N-terminal huntingtin: their role in suppression of aggregation and cellular toxicity", Hum. Mol. Genet., 9: 2009-2018.
Johnson et al., 1997, "Protein folding in vivo: unraveling complex pathways", Cell. 90(2): 201-204.
Kieran et al., 2004, "Treatment with arimoclomol, a coinducer of heat shock proteins, delays disease progression in ALS mice", Nature Medicine, 10: 402-405.
Kitamura et al., 2006, "Cytosolic chaperonin prevents polyglutamine toxicity with altering the aggregation state", Nat. Cell Biol., 8(10): 1163-1170.

Galam et al., 2007, "High-throughput assay for the identification of Hsp90 inhibitors based on Hsp90-dependent refolding of firefly luciferase", Bioorganic & Medicinal Chemistry, 15(5): 1939-1946.
Lindquist et al., 1988, "The heat-shock proteins", Ann. Rev. Genet., 22: 631-677.
Lindquist, 1992, "Heat-shock proteins and stress tolerance in microorganisms", Curr. Opinion Genet. Dev. 2: 748-755.
Morimoto, 2006, "Stress, aging, and neurodegenerative disease", New England J. Med., 355: 2254-2255.
Morley et al., 2004, "Regulation of longevity in Caenorhabditis elegans by heat shock factor and molecular chaperones", Mol. Biol. Cell, 15: 657-664.
Muchowski et al., 2000, "Hsp70 and hsp40 chaperones can inhibit self-assembly of polyglutamine proteins into amyloid-like fibrils", Proc. Natl. Acad. Sci. USA, 97: 7841-7846.
Muchowski, 2002, "Protein misfolding, amyloid formation, and neurodegeneration: a critical role for molecular chaperones", Neuron, 35: 9-12.
Neef et al., 2010, "Modulation of heat shock transcription factor 1 as a therapeutic target for small molecule intervention in neurodegenerative disease", Plos Biology, 8: e1000291.
Ohta et al., 2008, "Imine derivatives as new potent and selective CB2 cannabinoid receptor agonists with an analgesic action", Bioorg. Med. Chem, 16: 1111-1124.
Auluck PK et al., 2002, "Chaperone suppression of alpha-synuclein toxicity in a Drosophila model for Parkinson's disease", Science, 295: 865-868.
Pirkkala et al., 2001, "Roles of the heat shock transcription factors in regulation of the heat shock response and beyond", FASEB J., 15: 1118-1131.
Rabindran et al., 1993, "Regulation of heat shock factor trimer formation: role of a conserved leucine zipper", Science, 259: 230-234.
Regan et al., 2002, "Pyrazole urea-based inhibitors of p38 MAP kinase: from lead compound to clinical candidate", J. Med. Chem, 45: 2994-3008.
Wu, 1995, "Heat shock transcription factors: structure and regulation", Ann. Rev. Cell Devel. Biol, 11:441-469.
Wyttenbach et al., "Effects of heat shock, heat shock protein 40 (HDJ-2), and proteasome inhibition on protein aggregation in cellular models of Huntington's disease", 2000, PNAS, 97: 2898-2903.
Yam et al., 2008, "Defining the TRiC/CCT interactome links chaperonin function to stabilization of newly made proteins with complex topologies", Nat. Struct. Mol. Biol., 15: 1255-1262.
Zou et al., 1998, "Repression of heat shock transcription factor HSF1 activation by HSP90 (HSP90 complex) that forms a stress-sensitive complex with HSF1", Cell, 94: 471-480.
Peruncheralathan, S., "Highly Regioselective Synthesis of 1-Aryl-3(or 5)-alkyl / aryl-5(or 3)-(N-cycloamino) pyrazoles," Journal of Organic Chemistry, Oct. 2005, vol. 70, pp. 9644-9647.
Trott, Amy, et al., "Activation of Heat Shock and Antioxidant Responses by the Natural Product Celastrol: Transcriptional Signatures of a Thiol-Targeted Molecule," Molecular Biology of the Cell, vol. 19, No. 3, Mar. 2008, pp. 1104-1112.
Batulan, Z, et al., "Induction of Multipole Heat Shock Proteins and Neuroprotection in a Primary Culture Model of Familial Amyotrophic Lateral Sclerosis," Neurobiology of Disease, Blackwell Scientific Publications, Oxford, GB, vol. 24, No. 2, Nov. 1, 2006, pp. 213-225.
Powers, et al., "Inhibitors of the heat shock response: Biology and pharmacology," FEBS Letters, Elsevier, Amsterdam, NL., vol. 581, No. 19, Jul. 31, 2007, pp. 3758-3769.
Westerheide, Sandy D., et al.: "Heat shock response modulators as therapeutic tools for diseases of protein conformation," Journal of Biological Chemistry, The American Society of Biological Chemists, Inc., US, vol. 280, No. 39, Sep. 1, 2005, pp. 33097-33100.
Leone, S., et al., "SAR and QSAR study on 2-aminothiazole derivatives, modulators of transcriptional repression in Huntington's disease," Bioorganic & Medicinal Chemistry, Pergamon, GB, vol. 16, No. 10, Mar. 30, 2008, pp. 5695-5703.

(56) References Cited

OTHER PUBLICATIONS

Neef, Daniel W., "Heat shock transcription factor 1 as a therapeutic target in neurodegenerative diseases," Nature Reviews Drug Discvoery, vol. 10, No. 12, Jan. 1, 2011, pp. 930-944.

Salehi A.H., et al., "AEG3482 Is an Antiapoptotic Compound that Inhibits Ju Kinase Activity and Cell Death Through Induced Expression of Heat Shock Protein 70," Chemistry and Biology, Current Biology, London, GB, vol. 13, No. 2., Feb. 1, 2006, pp. 213-223.

* cited by examiner

US 9,156,775 B2

SUBSTITUTED 1,3-THIAZOLES AS HEAT SHOCK TRANSCRIPTION FACTOR 1 ACTIVATORS

CROSS REFERENCE TO RELATED APPLICATIONS

This application is a U.S. 371 National Phase Entry of International Patent Application No. PCT/US2011/059741, filed Nov. 8, 2011, which is a continuation of pending U.S. patent application Ser. No. 12/945,522, filed Nov. 12, 2010, the contents of which are incorporated by reference in their entireties.

STATEMENT REGARDING FEDERALLY SPONSORED RESEARCH OR DEVELOPMENT

This invention was made with government support under Grant Nos. GM059911-08 and GM076954 awarded by the National Institutes of Health. The government has certain rights in the invention.

FIELD OF THE INVENTION

The present invention relates to heat shock transcription factor, "HSF" activating compounds, methods for their discovery, and their research and therapeutic uses. In particular, the present invention provides compounds capable of facilitating HSF1 activation, and methods of using such compounds as therapeutic agents to treat a number of conditions associated with protein misfolding.

BACKGROUND OF THE INVENTION

For a long time, protein folding was regarded as simply a theoretical problem. Researchers investigated the mechanisms of protein folding to close the huge gap in our knowledge between the genetic blueprint of a protein and its biological function. Only in the 1990s did it become clear that wrongly folded proteins are involved in the development of many diseases. Protein folding has become a focus of attention in pharmaceutical research; it is probable that new approaches to the treatment of diseases such as Parkinson's disease and Alzheimer's disease are to be found within its convoluted pathways.

Protein folding diseases can be divided into two groups: in the first, excessive quantities of wrongly folded proteins collect in the form of uncontrolled piles of molecular rubbish. This is a group of diseases known as amyloidoses, of which Alzheimer's disease is the best-known example. In the other, a small error in the genetic blueprint leads to incomplete folding of a protein, which affects its function.

A common characteristic of all amyloidoses is the collection of plaques of insoluble protein in the extracellular tissue, which cannot be broken down by enzymes. Their ordered structure gives them crystal-like properties; they are made up of long filaments (fibrils) that are formed from densely packed-pleated sheets of identical proteins. There are about 20 different proteins that can act as the building blocks of these fibrils, each of which is associated with a different disease. In so-called systemic amyloidoses, the precursors of these plaques are transported through the bloodstream from their point of origin to their point of deposition. Localized amyloidoses are of greater clinical significance, as they mainly affect the central nervous system, the extracellular tissue of which is particularly susceptible to damage.

SUMMARY OF THE INVENTION

The present invention relates to HSF activating compounds, methods for their discovery, and their research and therapeutic uses. In particular, the present invention provides compounds capable of facilitating HSF1 activation, and methods of using such compounds as therapeutic agents to treat a number of conditions associated with protein misfolding. Thus, the present invention provides the needed, but until now, unrealized, improved compositions and methods for treating diseases associated with improper protein clearance Experiments conducted during the course of development of embodiments for the present invention developed a specialized high throughput screen for identifying small molecules capable of activating the human Heat Shock Transcription Factor 1 (HSF1) protein from complex chemical libraries. In addition, experiments conducted during the course of developing embodiments for the present invention identified molecules capable of activating the human Heat Shock Transcription Factor 1. It was shown that these molecules activate human HSF1.

As such, in certain embodiments, the present invention provides compositions capable of HSF activation. The compositions are not limited to a particular type of HSF. In some embodiments, the HSF is HSF1, HSF2 or HSF4. The compositions are not limited by the manner in which they result in HSF activation. In some embodiments, HSF activation includes, but is not limited to, activation of HSF1 homotrimerization, activation of HSF target gene expression (e.g., Heat Shock Elements), activation of HSF target protein expression (e.g., Heat Shock Proteins), and/or activation of protein chaperone activity (e.g., increased protein folding, increased protein solubilization, protein degradation).

In certain embodiments, the present invention provides compositions capable of HSF activation. For example, in some embodiments, the composition comprises a compound (e.g., a compound capable of HSF activation) described by, but not limited to, Formulas I, II, III, IV, V, VI, VII, VIII, IX, X, XI, and XI.

In some embodiments, the compound capable of HSF activation is described by the following Formula I:

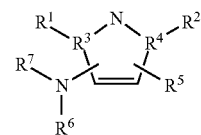

wherein $R^1$ and $R^2$ are independently chosen from: hydrogen; an optionally substituted saturated or unsaturated alkyl; $S(O)_{1-2}R^8$; $SO_2NR^8R^9$; $C(O)R^9$; $C(O)OR^8$; $C(O)NR^8R^9$; a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^B$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;

wherein $R^8$ and $R^9$ are independently chosen from hydrogen; an optionally substituted saturated or unsaturated alkyl; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents (e.g., a saturated or unsaturated, substituted or unsubstituted alkyl moeity or aryl moeity);
wherein

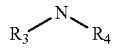

is either

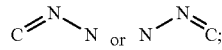

wherein $R^5$ is independently chosen from hydrogen, halogen, and cyano; an optionally substituted saturated or unsaturated alkyl; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;

wherein $R^6$ and $R^7$ are independently chosen from hydrogen; an optionally substituted saturated or unsaturated alkyl; $S(O)_{1-2}R^8$, $SO_2NR^8R^9$, $C(O)R^9$, $C(O)OR^8$, and $C(O)NR^8R^9$; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;

and pharmaceutically acceptable salts, solvates, chelates, non-covalent complexes, prodrugs, and mixtures thereof, including both R and S enantiomeric forms and racemic mixtures thereof.

In some embodiments, the compound of Formula I is a compound of Formula II:

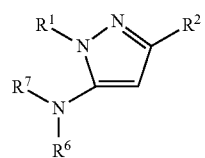

II wherein $R^1$ is hydrogen; an unsubstituted or substituted, saturated or unsaturated alkyl group selected from the group consisting of methyl, tert-butyl, $(CH_2)_2C(O)NH_2$, and $(CH_2)_3OCH_3$; an unsubstituted or substituted cycloalkyl, heterocycloalkyl, aryl, or heteroaryl group selected from the group consisting of cyclohexyl, phenyl, and thienyl; or an optionally substituted aryl or heteroaryl ring with 1-3 substituents independently selected from the group consisting of methyl, ethyl, propyl, butyl, F, Cl, $OCH_3$, $C(O)OCH_3$, CN, $C(O)NH_2$, $N(CH_3)_2$, $OC(O)CH_3$, and OH;

wherein $R^2$ is a substituted or unsubstituted saturated or unsaturated alkyl group selected from the group consisting of methyl, $CF_3$, tert-butyl, $(CH_2)_2C(O)NH_2$, and $(CH_2)_3OCH_3$; an optionally substituted cycloalkyl, heterocycloalkyl, aryl, or heteroaryl group selected from the group consisting of a cyclohexyl, phenyl, and thienyl; or an optionally substituted aryl or heteroaryl ring with 1-3 substituents independently selected from the group consisting of methyl, Cl, $OCH_3$, $C(O)OCH_3$, CN, $C(O)NH_2$, $N(CH_3)_2$, $OC(O)CH_3$, and OH;

wherein $R^6$ and $R^7$ are independently chosen from hydrogen; a substituted or unsubstituted saturated or unsaturated alkyl, aryl, or heteroaryl; and $S(O)_2R^8$ or $C(O)R^9$;

wherein $R^8$ is independently chosen from a substituted or unsubstituted saturated or unsaturated alkyl group selected from the group consisting of methyl, tert-butyl, $CF_3$, $(CH_2)$phenyl, $(CH_2)_3Oaryl$, $N(CH_3)_2$, $(CH_2)_2CF_3$, and $(CH_2)_2C(O)OCH_3$; a substituted or unsubstituted cycloalkyl or heterocycloalkyl ring selected from the group consisting of cyclohexyl and pyranoyl; an unsubstituted aryl ring having 0-3 heteroatoms independently selected from nitrogen, oxygen, or sulfur moiety selected from the group consisting of phenyl, pyridyl, and thienyl; and an aryl or heteroaryl ring optionally substituted with 1-3 substituents independently selected from the group consisting of methyl, ethyl, propyl, butyl, phenyl, F, $OCH_3$, Ophenyl, $CF_3$, $OCF_3$, CN, $NHC(O)CH_3$, $C(O)OH$, $S(O)_2CH_3$, $C(O)OCH_3$, F, Cl, Obutyl, $C(O)NH_2$, OH, $OC(O)CH_3$, and $C(O)OCH_3$;

wherein $R^9$ is independently chosen from a substituted or unsubstituted saturated or unsaturated alkyl group selected from the group consisting of $(CH_2)$thienyl, $(CH_2)O(CH_2)$phenyl, and $(CH_2)$aryl; and an aryl or heteroaryl ring optionally substituted with 0-2 substituents independently selected from the group consisting of butyl and $OCH_3$.

In some embodiments, the compounds of Formula I and/or Formula II include, but are not limited to, the following group:
1) N-(3-tert-Butyl-1-phenyl-1H-pyrazol-5-yl)-2-(thiophen-2-yl)acetamide,
2) 2-(Benzyloxy)-N-(3-tert-butyl-1-p-tolyl-1H-pyrazol-5-yl)acetamide,
3) 2-(Benzyloxy)-N-(3-tert-butyl-1-(4-chlorophenyl)-1H-pyrazol-5-yl)acetamide,
4) N-(1,3-Bis(4-chlorophenyl)-1H-pyrazol-5-yl)-4-butylbenzamide,
5) 2-Methoxy-N-(3-(4-methoxyphenyl)-1-p-tolyl-1H-pyrazol-5-yl)benzamide,
6) 4-Butyl-N-(3-phenyl-1-o-tolyl-1H-pyrazol-5-yl)benzamide,
7) 4-Butyl-N-(1-butyl-3-(4-chlorophenyl)-1H-pyrazol-5-yl)benzamide,
8) N-(3-(4-Chlorophenyl)-1-(4-methoxyphenyl)-1H-pyrazol-5-yl)-2-(3-methoxyphenyl)acetamide,
9) 2-(Benzyloxy)-N-(3-(4-methoxyphenyl)-1-o-tolyl-1H-pyrazol-5-yl)acetamide,
10) 4-Butyl-N-(4-butylbenzoyl)-N-(3-phenyl-1-o-tolyl-1H-pyrazol-5-yl)benzamide,
11) 4-Butyl-N-(3-(thiophen-2-yl)-1-o-tolyl-1H-pyrazol-5-yl)benzenesulfonamide,
12) N-(1,3-Diphenyl-1H-pyrazol-5-yl)-4-ethylbenzenesulfonamide,
13) 4-Ethyl-N-(3-(4-methoxyphenyl)-1-p-tolyl-1H-pyrazol-5-yl)benzenesulfonamide,
14) 4-Ethyl-N-(1-phenyl-3-(thiophen-2-yl)-1H-pyrazol-5-yl)benzenesulfonamide,
15) N-(1-(2-Fluorophenyl)-3-phenyl-1H-pyrazol-5-yl)-4-methoxybenzenesulfonamide,
16) N-(3-tert-Buyl-1-(2-fluorophenyl)-1H-pyrazol-5-yl)-4-ethylbenzenesulfonamide,
17) 4-Ethyl-N-(4-ethylphenylsulfonyl)-N-(1-phenyl-3-(thiophen-2-yl)-1H-pyrazol-5-yl)benzenesulfonamide, 18) 4-Butyl-N-(4-butylphenylsulfonyl)-N-(3-(thiophen-2-yl)-1-o-tolyl-1H-pyrazol-5-yl)benzenesulfonamide,
19) 4-Fluoro-N-(4-fluorophenylsulfonyl)-N-(3-(4-methoxyphenyl)-1-p-tolyl-1H-pyrazol-5-yl)benzenesulfonamide,
20) N-(3-(Thiophen-2-yl)-1-o-tolyl-1H-pyrazol-5-yl)methanesulfonamide,
21) Trifluoro-N-(3-(thiophen-2-yl)-1-o-tolyl-1H-pyrazol-5-yl)methanesulfonamide,
22) 3,3,3-Trifluoro-N-(3-(thiophen-2-yl)-1-o-tolyl-1H-pyrazol-5-yl)propane-1-sulfonamide,
23) 2-Methyl-N-(3-(thiophen-2-yl)-1-o-tolyl-1H-pyrazol-5-yl)propane-2-sulfonamide,
24) Methyl 3-(N-(3-(thiophen-2-yl)-1-o-tolyl-1H-pyrazol-5-yl)sulfamoyl)propanoate,
25) N-(3-(Thiophen-2-yl)-1-o-tolyl-1H-pyrazol-5-yl)cyclohexanesulfonamide,
26) N-(3-(Thiophen-2-yl)-1-o-tolyl-1H-pyrazol-5-yl)-tetrahydro-2H-pyran-4-sulfonamide,
27) Phenyl-N-(3-(thiophen-2-yl)-1-o-tolyl-1H-pyrazol-5-yl)methanesulfonamide,
28) 3-(4-Methoxyphenoxy)-N-(3-(thiophen-2-yl)-1-o-tolyl-1H-pyrazol-5-yl)propane-1-sulfonamide,
29) N-(3-(Thiophen-2-yl)-1-o-tolyl-1H-pyrazol-5-yl)thiophene-2-sulfonamide,
30) N-(3-(Thiophen-2-yl)-1-o-tolyl-1H-pyrazol-5-yl)thiazole-2-sulfonamide,
31) N-(3-(Thiophen-2-yl)-1-o-tolyl-1H-pyrazol-5-yl)pyridine-3-sulfonamide,
32) N-(3-(Thiophen-2-yl)-1-o-tolyl-1H-pyrazol-5-yl)pyridine-2-sulfonamide,
33) N-(3-(Thiophen-2-yl)-1-o-tolyl-1H-pyrazol-5-yl)benzenesulfonamide,
34) 4-Methyl-N-(3-(thiophen-2-yl)-1-o-tolyl-1H-pyrazol-5-yl)benzenesulfonamide,
35) 4-Ethyl-N-(3-(thiophen-2-yl)-1-o-tolyl-1H-pyrazol-5-yl)benzenesulfonamide,
36) N-(3-(Thiophen-2-yl)-1-o-tolyl-1H-pyrazol-5-yl)biphenyl-4-sulfonamide,
37) 4-Phenoxy-N-(3-(thiophen-2-yl)-1-o-tolyl-1H-pyrazol-5-yl)benzenesulfonamide,
38) N-(3-(Thiophen-2-yl)-1-o-tolyl-1H-pyrazol-5-yl)-4-(trifluoromethyl)benzenesulfonamide,
39) N-(3-(Thiophen-2-yl)-1-o-tolyl-1H-pyrazol-5-yl)-4-(trifluoromethoxy)benzenesulfonamide,
40) 4-Cyano-N-(3-(thiophen-2-yl)-1-o-tolyl-1H-pyrazol-5-yl)benzenesulfonamide,
41) N-(4-(N-(3-(Thiophen-2-yl)-1-o-tolyl-1H-pyrazol-5-yl)sulfamoyl)phenyl)acetamide,
42) 4-(N-(3-(Thiophen-2-yl)-1-o-tolyl-1H-pyrazol-5-yl)sulfamoyl)benzoic acid
43) 4-(Methylsulfonyl)-N-(3-(thiophen-2-yl)-1-o-tolyl-1H-pyrazol-5-yl)benzenesulfonamide,
44) 4-Acetyl-N-(3-(thiophen-2-yl)-1-o-tolyl-1H-pyrazol-5-yl)benzenesulfonamide,
45) 4-Methoxy-N-(3-(thiophen-2-yl)-1-o-tolyl-1H-pyrazol-5-yl)benzenesulfonamide,
46) 4-Fluoro-N-(3-(thiophen-2-yl)-1-o-tolyl-1H-pyrazol-5-yl)benzenesulfonamide,
47) 4-Chloro-N-(3-(thiophen-2-yl)-1-o-tolyl-1H-pyrazol-5-yl)benzenesulfonamide,
48) 2,6-Difluoro-N-(3-(thiophen-2-yl)-1-o-tolyl-1H-pyrazol-5-yl)benzenesulfonamide,
49) 4-Butoxy-N-(3-(thiophen-2-yl)-1-o-tolyl-1H-pyrazol-5-yl)benzenesulfonamide,
50) 4-(N-(3-(Thiophen-2-yl)-1-o-tolyl-1H-pyrazol-5-yl)sulfamoyl)benzamide,
60) 4-Hydroxy-N-(3-(thiophen-2-yl)-1-o-tolyl-1H-pyrazol-5-yl)benzenesulfonamide,
61) 4-(N-(3-(Thiophen-2-yl)-1-o-tolyl-1H-pyrazol-5-yl)sulfamoyl)phenyl acetate,
62) Methyl 4-(N-(3-(thiophen-2-yl)-1-o-tolyl-1H-pyrazol-5-yl)sulfamoyl)benzoate,
63) 4-Butyl-N-(3-methyl-1-o-tolyl-1H-pyrazol-5-yl)benzenesulfonamide,
64) 4-Butyl-N-(3-tert-butyl-1-o-tolyl-1H-pyrazol-5-yl)benzenesulfonamide,
65) 4-Butyl-N-(1-o-tolyl-3-(trifluoromethyl)-1H-pyrazol-5-yl)benzenesulfonamide,
66) 3-(5-(4-Butylphenylsulfonamido)-1-o-tolyl-1H-pyrazol-3-yl)propanamide,
67) 4-Butyl-N-(3-(3-methoxypropyl)-1-o-tolyl-1H-pyrazol-5-yl)benzenesulfonamide,
68) 4-Butyl-N-(3-cyclohexyl-1-o-tolyl-1H-pyrazol-5-yl)benzenesulfonamide,
70) 4-Butyl-N-(3-phenyl-1-o-tolyl-1H-pyrazol-5-yl)benzenesulfonamide,
71) 4-Butyl-N-(3-(4-methoxyphenyl)-1-o-tolyl-1H-pyrazol-5-yl)benzenesulfonamide,
72) 4-Butyl-N-(3-(2-methoxyphenyl)-1-o-tolyl-1H-pyrazol-5-yl)benzenesulfonamide,
73) 4-Butyl-N-(3-(2,4-dichlorophenyl)-1-o-tolyl-1H-pyrazol-5-yl)benzenesulfonamide,
74) Methyl 4-(5-(4-butylphenylsulfonamido)-1-o-tolyl-1H-pyrazol-3-yl)benzoate,
75) 4-Butyl-N-(3-(4-cyanophenyl)-1-o-tolyl-1H-pyrazol-5-yl)benzenesulfonamide,
76) 4-Butyl-N-(3-(4-(dimethylamino)phenyl)-1-o-tolyl-1H-pyrazol-5-yl)benzenesulfonamide,
77) 4-(5-(4-Butylphenylsulfonamido)-1-o-tolyl-1H-pyrazol-3-yl)phenyl acetate,
78) 4-Butyl-N-(3-(4-hydroxyphenyl)-1-o-tolyl-1H-pyrazol-5-yl)benzenesulfonamide,
79) 4-(5-(4-Butylphenylsulfonamido)-1-o-tolyl-1H-pyrazol-3-yl)benzamide,
80) 4-Butyl-N-(3-(thiophen-2-yl)-1H-pyrazol-5-yl)benzenesulfonamide,
81) 4-Butyl-N-(1-methyl-3-(thiophen-2-yl)-1H-pyrazol-5-yl)benzenesulfonamide,
82) 4-Butyl-N-(1-tert-butyl-3-(thiophen-2-yl)-1H-pyrazol-5-yl)benzenesulfonamide,
83) 3-(5-(4-Butylphenylsulfonamido)-3-(thiophen-2-yl)-1H-pyrazol-1-yl)propanamide,
84) 4-Butyl-N-(1-(3-methoxypropyl)-3-(thiophen-2-yl)-1H-pyrazol-5-yl)benzenesulfonamide,
85) 4-Butyl-N-(1,3-di(thiophen-2-yl)-1H-pyrazol-5-yl)benzenesulfonamide,
86) 4-Butyl-N-(1-cyclohexyl-3-(thiophen-2-yl)-1H-pyrazol-5-yl)benzenesulfonamide,
87) 4-Butyl-N-(1-phenyl-3-(thiophen-2-yl)-1H-pyrazol-5-yl)benzenesulfonamide,
88) 4-Butyl-N-(3-(thiophen-2-yl)-1-p-tolyl-1H-pyrazol-5-yl)benzenesulfonamide,
90) 4-Butyl-N-(1-(2,4-dichlorophenyl)-3-(thiophen-2-yl)-1H-pyrazol-5-yl)benzenesulfonamide,
91) 4-Butyl-N-(1-(2-methoxyphenyl)-3-(thiophen-2-yl)-1H-pyrazol-5-yl)benzenesulfonamide,
92) 4-Butyl-N-(1-(4-methoxyphenyl)-3-(thiophen-2-yl)-1H-pyrazol-5-yl)benzenesulfonamide,
93) N-(1-(Biphenyl-4-yl)-3-(thiophen-2-yl)-1H-pyrazol-5-yl)-4-butylbenzenesulfonamide,
94) 4-Butyl-N-(1-(4-ethylphenyl)-3-(thiophen-2-yl)-1H-pyrazol-5-yl)benzenesulfonamide, 95) Methyl 4-(5-(4-butylphenylsulfonamido)-3-(thiophen-2-yl)-1H-pyrazol-1-yl)benzoate,
96) 4-Butyl-N-(1-(4-cyanophenyl)-3-(thiophen-2-yl)-1H-pyrazol-5-yl)benzenesulfonamide,
97) 4-(5-(4-Butylphenylsulfonamido)-3-(thiophen-2-yl)-1H-pyrazol-1-yl)benzamide,
98) 4-Butyl-N-(1-(4-(dimethylamino)phenyl)-3-(thiophen-2-yl)-1H-pyrazol-5-yl)benzenesulfonamide,
99) 4-(5-(4-Butylphenylsulfonamido)-3-(thiophen-2-yl)-1H-pyrazol-1-yl)phenyl acetate,
100) 4-Butyl-N-(1-(4-hydroxyphenyl)-3-(thiophen-2-yl)-1H-pyrazol-5-yl)benzenesulfonamide, and
101) 4-Butyl-N-(1-(4-butylphenyl)-3-(thiophen-2-yl)-1H-pyrazol-5-yl)benzenesulfonamide.

In some embodiments, the compound capable of HSF activation is described by the following Formula III:

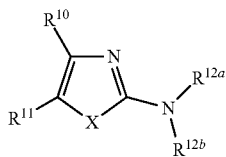

III wherein X is O, S, or $NR^{12c}$;
wherein $R^{10}$ and $R^{11}$ are either A) independently chosen from hydrogen; halogen; cyano; nitro; an optionally substituted saturated or unsaturated alkyl; $OR^8$; $OC(O)R^8$; $NR^8R^9$; $S(O)_{1-2}R^8$; $SO_2NR^8R^9$; $NR^8SO_2R^9$; $C(O)R^9$; $C(O)OR^8$; $C(O)NR^8R^9$; $NR^8C(O)R^9$; $NR^8C(O)OR^9$; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro; or B) optionally together with the atom to which $R^{10}$ and $R^{11}$ are attached form one or more substituted or unsubstituted cycloalkyl, cycloaryl, cycloheteroalkyl, or heteroaryl rings;
wherein $R^8$ and $R^9$ are independently chosen from hydrogen, an optionally substituted saturated or unsaturated alkyl; and a saturated or unsaturated, aromatic or non-aromatic, 3-8 membered monocyclic ring, or 8-12 bicyclic membered ring, having 0-3 heteroatoms independently selected from nitrogen, oxygen, or sulfur, optionally substituted with 1-5 substituents (e.g., a saturated or unsaturated, substituted or unsubstituted alkyl moiety or aryl moiety);
wherein $R^{12a}$, $R^{12b}$ and $R^{12c}$ are independently chosen from hydrogen; an optionally substituted saturated or unsaturated alkyl; $S(O)_{1-2}R^8$, $SO_2NR^8R^9$, $C(O)R^9$, $C(O)OR^8$, and $C(O)NR^8R^9$; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;
and pharmaceutically acceptable salts, solvates, chelates, non-covalent complexes, prodrugs, and mixtures thereof, including both R and S enantiomeric forms and racemic mixtures thereof.

In some embodiments, the compound of Formula III is a compound of Formula IV:

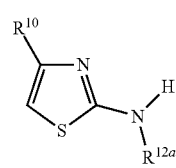

IV wherein $R^{10}$ is independently chosen from hydrogen; an unsubstituted or substituted saturated alkyl group selected from the group consisting of methyl, ethyl, $CF_3$, tert-butyl, $(CH_2)_2C(O)NH_2$, and $(CH_2)_3OCH_3$; an unsubstituted or substituted cycloalkyl, heterocycloalkyl, aryl, or heteroaryl group selected from the group consisting of cyclohexyl and phenyl; and an aryl ring having 0-3 heteroatoms independently selected from nitrogen, oxygen, or sulfur selected from the group consisting of thienyl and pyridyl; and an aryl or heteroaryl ring optionally substituted with 1-3 substituents independently selected from the group consisting of methyl, ethyl, butyl, tert-butyl, phenyl, $OCH_3$, OH, CN, F, Cl, $N(CH_3)_2$, $C(O)NH_2$, $OC(O)CH_3$, and $C(O)OCH_3$;
wherein $R^{12a}$ is $C(O)R^9$; an optionally substituted, saturated or unsaturated alkyl group selected from the group consisting of methyl, $CF_3$, tert-butyl, $(CH_2)_2C(O)NH_2$, $(CH_2)_3OCH_3$, $(CH_2)_2CF_3$, and $CH_2$-phenyl; cyclohexyl or phenyl; or an aryl ring having 0-3 heteroatoms independently selected from nitrogen, oxygen, or sulfur selected from the group consisting of isoxazolyl, pyridyl, and thienyl; or an aryl or heteroaryl ring optionally substituted with 1-2 substituents independently selected from the group consisting of methyl, ethyl, butyl, OH, F, $N(CH_3)_2$, Cl, $CF_3$, $OCH_3$, CN, C(O)OH, $C(O)CH_3$, Ophenyl, $OCF_3$, $NO_2$, $NHC(O)CH_3$, phenyl, $C(O)OCH_3$, $S(O)_2CH_3$, $C(O)NH_2$, Obutyl, $OC(O)CH_3$, $(CH_2)_3OAr$, Opyridyl, and $(CH_2)$pipiridinyl;
wherein $R^9$ is an unsubstituted or substituted heterocloalkyl, aryl or heteroaryl group.

In some embodiments, the compounds of Formula III and/or Formula IV include, but are not limited to, the following group:
102) $N^1$-(4-(2,4-Dimethoxyphenyl)thiazol-2-yl)-$N^4$,$N^4$-dimethylbenzene-1,4-diamine,
103) N-(2,6-Dichlorophenyl)-4-(trifluoromethyl)thiazol-2-amine,
104) $N^1$-(4-(3-Methoxyphenyl)thiazol-2-yl)-$N^4$,$N^4$-dimethylbenzene-1,4-diamine,
105) $N^1$,$N^1$-Dimethyl-$N^4$-(4-phenylthiazol-2-yl)benzene-1,4-diamine,
106) 1-(4-(4-(Trifluoromethyl)thiazol-2-ylamino)phenyl)ethanone,
107) $N^1$,$N^1$-Dimethyl-$N^4$-(4-(trifluoromethyl)thiazol-2-Abenzene-1,4-diamine,
108) N-(4-Nitrophenyl)-4-(trifluoromethyl)thiazol-2-amine,
109) $N^1$-(4-(Biphenyl-4-yl)thiazol-2-yl)-$N^4$,$N^4$-dimethylbenzene-1,4-diamine,
110) N-(2-chlorophenyl)-4-(2,4-dimethoxyphenyl)thiazol-2-amine,
111) 1-(4-(4-(4-Fluorophenyl)thiazol-2-ylamino)phenyl)ethanone,
112) 4-Ethyl-N-(4-nitrophenyl)thiazol-2-amine,
113) 4-(4-(Trifluoromethyl)thiazol-2-ylamino)phenol,
114) N-(2,6-Dichlorophenyl)-4-phenylthiazol-2-amine,
115) 4-(Biphenyl-4-yl)-N-(2-chlorophenyl)thiazol-2-amine,
116) N-(4-(3-Methoxyphenyl)thiazol-2-yl)benzamide, 117) N-(4-Phenylthiazol-2-yl)benzamide,
118) N-(4-(2,4-Dimethoxyphenyl)thiazol-2-yl)benzamide,
119) N-Methyl-4-phenylthiazol-2-amine,
120) N-tert-Butyl-4-phenylthiazol-2-amine,
121) N-(3-Methoxypropyl)-4-phenylthiazol-2-amine,
122) N-Benzyl-4-phenylthiazol-2-amine,
123) 3-(4-Phenylthiazol-2-ylamino)propanamide,
124) 4-Phenyl-N-(trifluoromethyl)thiazol-2-amine,
125) 4-Phenyl-N-(3,3,3-trifluoropropyl)thiazol-2-amine,
126) N-(3-(4-Methoxyphenoxy)propyl)-4-phenylthiazol-2-amine,
127) 4-Phenyl-N-(thiophen-2-yl)thiazol-2-amine,
128) 4-Phenyl-N-(thiazol-2-yl)thiazol-2-amine,
129) N-Cyclohexyl-4-phenylthiazol-2-amine,
130) N-4-Diphenylthiazol-2-amine,
131) N-(4-Butylphenyl)-4-phenylthiazol-2-amine,
132) N-(4-Ethylphenyl)-4-phenylthiazol-2-amine,
133) 4-(4-Phenylthiazol-2-ylamino)phenol,
134) N-(4-Fluorophenyl)-4-phenylthiazol-2-amine,
135) N-(4-Chlorophenyl)-4-phenylthiazol-2-amine,
136) 4-Phenyl-N-(4-(trifluoromethyl)phenyl)thiazol-2-amine,
137) N-(2,6-Difluorophenyl)-4-phenylthiazol-2-amine,
138) N-(4-Methoxyphenyl)-4-phenylthiazol-2-amine,
139) 4-(4-Phenylthiazol-2-ylamino)benzonitrile,
140) 4-(4-Phenylthiazol-2-ylamino)benzoic acid,
141) 1-(4-(4-Phenylthiazol-2-ylamino)phenyl)ethanone,
142) 4-Phenyl-N-(pyridin-4-yl)thiazol-2-amine,
143) N-(4-Phenoxyphenyl)-4-phenylthiazol-2-amine,
144) 4-Phenyl-N-(4-(trifluoromethoxy)phenyl)thiazol-2-amine,
145) N-(4-(4-Phenylthiazol-2-ylamino)phenyl)acetamide,
146) 4-Phenyl-N-p-tolylthiazol-2-amine,
147) 4-Phenyl-N-o-tolylthiazol-2-amine,
148) N-(Biphenyl-4-yl)-4-phenylthiazol-2-amine,
149) N-(4-((4-Methylpiperazin-1-yl)methyl)phenyl)-4-phenylthiazol-2-amine,
150) Methyl 4-(4-phenylthiazol-2-ylamino)benzoate,
151) N-(4-(Methylsulfonyl)phenyl)-4-phenylthiazol-2-amine,
152) 4-(4-Phenylthiazol-2-ylamino)benzamide,
153) N-(4-Butoxyphenyl)-4-phenylthiazol-2-amine,
154) 4-(4-Phenylthiazol-2-ylamino)phenyl acetate,
155) 4-Phenyl-N-(4-(pyridin-3-yloxy)phenyl)thiazol-2-amine,
156) $N^1,N^1$-Dimethyl-$N^4$-(thiazol-2-yl)benzene-1,4-diamine,
157) $N^1,N^1$-Dimethyl-$N^4$-(4-methylthiazol-2-yl)benzene-1,4-diamine,
158) $N^1$-(4-tert-Butylthiazol-2-yl)-$N^4,N^4$-dimethylbenzene-1,4-diamine,
159) 3-(2-(4-(Dimethylamino)phenylamino)thiazol-4-yl)propanamide,
160) $N^1$-(4-(3-Methoxypropyl)thiazol-2-yl)-$N^4,N^4$-dimethylbenzene-1,4-diamine,
161) $N^1$-(4-Cyclohexylthiazol-2-yl)-$N^4,N^4$-dimethylbenzene-1,4-diamine,
162) $N^1$-(4-(4-Methoxyphenyl)thiazol-2-yl)-$N^4,N^4$-dimethylbenzene-1,4-diamine,
163) 4-(2-(4-(Dimethylamino)phenylamino)thiazol-4-yl)phenol,
164) $N^1,N^1$-Dimethyl-$N^4$-(4-o-tolylthiazol-2-yl)benzene-1,4-diamine,
165) $N^1$-(4-(2-Methoxyphenyl)thiazol-2-yl)-$N^4,N^4$-dimethylbenzene-1,4-diamine,
166) 4-(2-(4-(Dimethylamino)phenylamino)thiazol-4-yl)benzonitrile,
167) $N^1$-(4-(2,4-Dichlorophenyl)thiazol-2-yl)-$N^4,N^4$-dimethylbenzene-1,4-diamine,
168) $N^1$-(4-(3,4-Dichlorophenyl)thiazol-2-yl)-$N^4,N^4$-dimethylbenzene-1,4-diamine,
169) $N^1,N^1$-Dimethyl-$N^4$-(4-(thiophen-2-yl)thiazol-2-yl)benzene-1,4-diamine,
170) $N^1,N^1$-Dimethyl-$N^4$-(4-(pyridin-4-yl)thiazol-2-yl)benzene-1,4-diamine,
171) $N^1,N^1$-Dimethyl-$N^4$-(4-p-tolylthiazol-2-yl)benzene-1,4-diamine,
172) $N^1$-(4-(4-Ethylphenyl)thiazol-2-yl)-$N^4,N^4$-dimethylbenzene-1,4-diamine,
173) $N^1$-(4-(4-Butylphenyl)thiazol-2-yl)-$N^4,N^4$-dimethylbenzene-1,4-diamine,
174) $N^1$-(4-(4-(Dimethylamino)phenyl)thiazol-2-yl)-$N^4,N^4$-dimethylbenzene-1,4-diamine,
175) 4-(2-(4-(Dimethylamino)phenylamino)thiazol-4-yl)benzamide,
176) 4-(2-(4-(Dimethylamino)phenylamino)thiazol-4-yl)phenyl acetate,
177) Methyl 4-(2-(4-(dimethylamino)phenylamino)thiazol-4-yl)benzoate, and
178) $N^1$-(4-(4-tert-Butylphenyl)thiazol-2-yl)-$N^4,N^4$-dimethylbenzene-1,4-diamine.

In some embodiments, the compound of Formula III is a compound of Formula V:

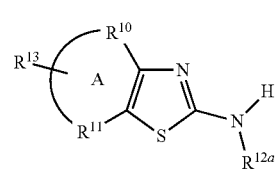

wherein A is $R^{10}$ and $R^{11}$ taken together to form a substituted or unsubstituted, unsaturated or partially unsaturated monocyclic or bicyclic 5-12 membered ring, or an aryl ring;
wherein $R^{12a}$ is independently hydrogen; $C(O)R^9$; an unsubstituted or substituted saturated alkyl group selected from the group consisting of methyl, $CF_3$, tert-butyl, $(CH_2)_2C(O)NH_2$, and $(CH_2)_3OCH_3$; cyclohexyl or phenyl; or an aryl ring having 0-3 heteroatoms independently selected from nitrogen, oxygen, or sulfur selected from the group consisting of thienyl and pyridyl; an aryl or heteroaryl ring optionally substituted with 1-3 substituents independently selected from the group consisting of methyl, ethyl, butyl, OH, F, $N(CH_3)_2$, Cl, F, $OCH_3$, CN, C(O)OH, $C(O)OCH_3$, phenyl, $C(O)NH_2$, and $OC(O)CH_3$;
wherein $R^9$ is a substituted or unsubstituted aryl or heteroaryl group;
wherein $R^{13}$ is hydrogen, a substituted or unsubstituted alkyl, heterocycloalkyl, aryl or heteroaryl group;
and pharmaceutically acceptable salts, solvates, chelates, non-covalent complexes, prodrugs, and mixtures thereof, including both R and S enantiomeric forms and racemic mixtures thereof.

In some embodiments, the compounds of Formula III and/or Formula IV include, but are not limited to, the following group:
179) 4-(Benzo[d]thiazol-2-ylamino)phenol,
180) $N^1$-(Benzo[d]thiazol-2-yl)-$N^4,N^4$-dimethylbenzene-1,4-diamine,
181) N-(8H-Indeno[1,2-d]thiazol-2-yl)benzamide,
182) 4-(8H-Indeno[1,2-d]thiazol-2-ylamino)phenol, 183) N-(2,6-Dichlorophenyl)-8H-indeno[1,2-d]thiazol-2-amine,
184) N¹-(8H-Indeno[1,2-d]thiazol-2-yl)-N⁴,N⁴-dimethylbenzene-1,4-diamine,
185) Benzo[d]thiazol-2-amine,
186) N-Methylbenzo[d]thiazol-2-amine,
187) N-(Trifluoromethyl)benzo[d]thiazol-2-amine,
188) N-tert-Butylbenzo[d]thiazol-2-amine,
189) N-(3-Methoxypropyl)benzo[d]thiazol-2-amine,
190) 3-(Benzo[d]thiazol-2-ylamino)propanamide,
191) N-(Thiophen-2-yl)benzo[d]thiazol-2-amine,
192) N-(Pyridin-4-yl)benzo[d]thiazol-2-amine,
193) N-Cyclohexylbenzo[d]thiazol-2-amine,
194) N-Phenylbenzo[d]thiazol-2-amine,
195) N-(4-Methoxyphenyl)benzo[d]thiazol-2-amine,
196) N-(2-Methoxyphenyl)benzo[d]thiazol-2-amine,
197) 4-(Benzo[d]thiazol-2-ylamino)benzonitrile,
198) N-(2,4-Dichlorophenyl)benzo[d]thiazol-2-amine,
199) 4-(Benzo[d]thiazol-2-ylamino)benzamide,
200) N-(3,4-Dichlorophenyl)benzo[d]thiazol-2-amine,
201) Methyl 4-(benzo[d]thiazol-2-ylamino)benzoate,
202) N-(Biphenyl-4-yl)benzo[d]thiazol-2-amine,
203) N-(4-Ethylphenyl)benzo[d]thiazol-2-amine,
204) N-p-Tolylbenzo[d]thiazol-2-amine,
205) N-o-Tolylbenzo[d]thiazol-2-amine,
206) N-(2,6-Difluorophenyl)benzo[d]thiazol-2-amine,
207) 4-(Benzo[d]thiazol-2-ylamino)benzoic acid,
208) N-(4-Butylphenyl)benzo[d]thiazol-2-amine, and
209) 4-(Benzo[d]thiazol-2-ylamino)phenyl acetate.

In some embodiments, the compound capable of HSF activation is described by the following Formula VI:

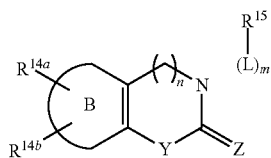

wherein n is 0 to 4;
wherein m is 0 to 5;
wherein L is substituted or unsubstituted C;
wherein Y is O, S, or NR¹⁶;
wherein Z is O or S;
wherein B is a saturated or unsaturated, aromatic or non-aromatic, 3-8 membered monocyclic ring, or 8-12 bicyclic membered ring, having 0-3 heteroatoms independently selected from nitrogen, oxygen, or sulfur;
wherein $R^{14a}$ and $R^{14b}$ are independently chosen from hydrogen; an optionally substituted group selected from a saturated or unsaturated alkyl; $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;
wherein $R^8$ and $R^9$ are independently chosen from hydrogen, an optionally substituted saturated or unsaturated alkyl; and a saturated or unsaturated, aromatic or non-aromatic, 3-8 membered monocyclic ring, or 8-12 bicyclic membered ring, having 0-3 heteroatoms independently selected from nitrogen, oxygen, or sulfur, optionally substituted with 1-5 substituents (e.g., a saturated or unsaturated, substituted or unsubstituted alkyl moeity or aryl moeity);
wherein $R^{15}$ and $R^{16}$ are independently hydrogen; an optionally substituted saturated or unsaturated alkyl; $S(O)_{1-2}R^8$, $SO_2NR^8R^9$, $C(O)R^9$, $C(O)OR^8$, $C(O)NR^8R^9$; or a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;

and pharmaceutically acceptable salts, solvates, chelates, non-covalent complexes, prodrugs, and mixtures thereof, including both R and S enantiomeric forms and racemic mixtures thereof.

In some embodiments, the compound of Formula VI is a compound of Formula VII:

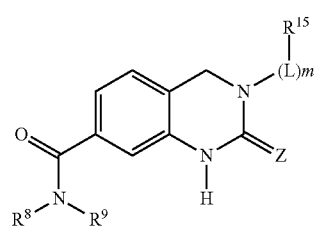

wherein m is 0 to 2;
wherein L is a substituted or unsubstituted C;
wherein Z is O or S;
wherein $R^8$, $R^9$, and $R^{15}$ are independently chosen from hydrogen, a substituted or unsubstituted alkyl, cycloalkyl, heterocycloalkyl, aryl, and heteroaryl.

In some embodiments, the compounds of Formula VI and/or Formula VII include, but are not limited to, the following group:
210) 2-Oxo-3-(2-(pyridin-2-yl)ethyl)-N-((tetrahydrofuran-2-yl)methyl)-1,2,3,4-tetrahydroquinazoline-7-carboxamide,
211) N-(4-Methoxybenzyl)-2-oxo-3-phenethyl-1,2,3,4-tetrahydroquinazoline-7-carboxamide, and
212) N-(4-Methoxybenzyl)-3-phenethyl-2-thioxo-1,2,3,4-tetrahydroquinazoline-7-carboxamide.

In some embodiments, the compound capable of HSF activation is described by the following Formula VIII:

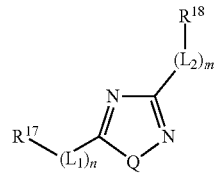

wherein Q is chosen from O, S and NR¹⁹;
wherein n and m are 0 to 5;
wherein $L_1$ and $L_2$ are substituted or unsubstituted C;
wherein $R^{17}$ and $R^{18}$ are independently chosen from hydrogen; an optionally substituted saturated or unsaturated alkyl; $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, and $NR^8C(O)OR^9$; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;

wherein $R^8$ and $R^9$ are independently chosen from hydrogen, an optionally substituted saturated or unsaturated alkyl; and a saturated or unsaturated, aromatic or non-aromatic, 3-8 membered monocyclic ring, or 8-12 bicyclic membered ring, having 0-3 heteroatoms independently selected from nitrogen, oxygen, or sulfur, optionally substituted with 1-5 substituents (e.g., a saturated or unsaturated, substituted or unsubstituted alkyl moiety or aryl moiety);

wherein $R^{19}$ is independently hydrogen; an optionally substituted group selected from a saturated or unsaturated alkyl; $S(O)_{1-2}R^8$, $SO_2NR^8R^9$, $C(O)R^9$, $C(O)OR^8$, and $C(O)NR^8R^9$; or a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;

and pharmaceutically acceptable salts, solvates, chelates, non-covalent complexes, prodrugs, and mixtures thereof, including both R and S enantiomeric forms and racemic mixtures thereof.

In some embodiments, the compound capable of HSF activation is described by the following Formula IX:

$$IX$$

wherein $R^9$ and $R^{18}$ are chosen from a substituted or unsubstituted alkyl, cycloalkyl, heterocycloalkyl, aryl, and heteroaryl;

and pharmaceutically acceptable salts, solvates, chelates, non-covalent complexes, prodrugs, and mixtures thereof, including both R and S enantiomeric forms and racemic mixtures thereof.

In some embodiments, the compounds of Formula IX include, but are not limited to, the following group:
213) 6-Chloro-N-((3-(3-fluorophenyl)-1,2,4-oxadiazol-5-yl)methyl)pyridin-3-amine,
214) 2-(5-Methoxy-1H-indol-3-yl)-N-((3-(naphthalen-2-yl)-1,2,4-oxadiazol-5-yl)methyl)ethanamine, and
215) 4-Methyl-N-((3-(4-nitrophenyl)-1,2,4-oxadiazol-5-yl)methyl)piperazin-1-amine.

In some embodiments, the compound capable of HSF activation is described by the following Formula X:

$$X$$

wherein m, p, and o are 0 to 5;
wherein n is 1 to 4;

wherein $L_3$, $L_4$, $L_5$, and $L_6$ are substituted or unsubstituted C;

wherein T is O, S, or $NR^{24}R^{25}$;

wherein $R^{20}$ and $R^{21}$ are independently chosen from hydrogen; an optionally substituted group selected from a saturated or unsaturated alkyl; $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, and $NR^8C(O)OR^9$; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;

wherein $R^{22}$ and $R^{23}$ are A) independently chosen from hydrogen; an optionally substituted group selected from a saturated or unsaturated alkyl; $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, and $NR^8C(O)OR^9$; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro; or B) together with the atom to which $R^{22}$ and $R^{23}$ are attached form one or more substituted or unsubstituted heterocycloalkyl, or heteroaryl rings;

wherein $R^{24}$ and $R^{25}$ are independently hydrogen; an optionally substituted saturated or unsaturated alkyl; $S(O)_{1-2}R^8$, $SO_2NR^8R^9$, $C(O)R^9$, $C(O)OR^8$, and $C(O)NR^8R^9$; and a saturated or unsaturated, aromatic or non-aromatic ring (e.g., a 3-8 membered monocyclic ring) (e.g., a 8-12 bicyclic membered ring) having 0-3 heteroatoms independently selected from nitrogen, oxygen, or sulfur, optionally substituted with 1-5 substituents independently selected from the group consisting of $R^8$, $OR^8$, $OC(O)R^8$, $NR^8R^9$, $S(O)_{1-2}R^8$, $SO_2NR^8R^9$, $NR^8SO_2R^9$, $C(O)R^9$, $C(O)OR^8$, $C(O)NR^8R^9$, $NR^8C(O)R^9$, $NR^8C(O)OR^9$, halogen, cyano, oxo, and nitro;

wherein $R^8$ and $R^9$ are independently chosen from hydrogen, an optionally substituted saturated or unsaturated alkyl; and a saturated or unsaturated, aromatic or non-aromatic, 3-8 membered monocyclic ring, or 8-12 bicyclic membered ring, having 0-3 heteroatoms independently selected from nitrogen, oxygen, or sulfur, optionally substituted with 1-5 substituents (e.g., a saturated or unsaturated, substituted or unsubstituted alkyl moiety or aryl moiety);

and pharmaceutically acceptable salts, solvates, chelates, non-covalent complexes, prodrugs, and mixtures thereof, including both R and S enantiomeric forms and racemic mixtures thereof.

In some embodiments, the compound of Formula X is a compound of Formula XI:

$$XI$$

wherein m is 1 to 2;
wherein $L_4$ is substituted or unsubstituted C;

wherein R$^{21}$ is chosen from a substituted or unsubstituted, partially saturated alkyl, cycloalkyl, or heterocycloalkyl; and a substituted or unsubstituted aryl or heteroaryl;

and pharmaceutically acceptable salts, solvates, chelates, non-covalent complexes, prodrugs, and mixtures thereof, including both R and S enantiomeric forms and racemic mixtures thereof.

In some embodiments, the compounds of Formula X and/or Formula XI include, but are not limited to, the following group:

216) N$^2$-(2-(Diethylamino)ethyl)-N$^1$-(3,4-dimethoxyphenethyl)-N$^2$-ethyl-1-phenylethane-1,2-diamine, and 217) N$^2$-(2-(Diethylamino)ethyl)-N$^2$-ethyl-N$^1$-(4-fluorobenzyl)-1-phenylethane-1,2-diamine In some embodiments, the compound of Formula X is a compound of Formula XII:

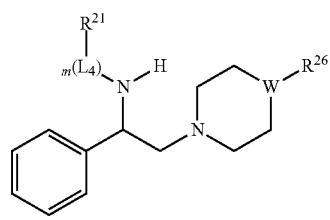

XII wherein m is 2 to 4;
wherein L$_4$ is substituted or unsubstituted C;
wherein W is N or C;
wherein R$^{21}$ is chosen from a substituted or unsubstituted alkyl, NR$^8$R$^9$, cycloalkyl, heterocycloalkyl, aryl, and heteroaryl;
wherein R$^{26}$ is chosen from a substituted or unsubstituted alkyl, cycloalkyl, heterocycloalkyl, aryl, and heteroaryl;

and pharmaceutically acceptable salts, solvates, chelates, non-covalent complexes, prodrugs, and mixtures thereof, including both R and S enantiomeric forms and racemic mixtures thereof.

In some embodiments, the compounds of Formula X and/or Formula XII include, but are not limited to, the following group:

218) N$^1$,N$^1$-Diethyl-N$^4$-(1-phenyl-2-(4-phenylpiperazin-1-yl)ethyl)pentane-1,4-diamine, and 219) 3-(Azepan-1-yl)-N-(2-(4-methylpiperidin-1-yl)-1-phenylethyl)propan-1-amine In certain embodiments, the present invention provides methods for treating (e.g., treating a subject ((e.g., a human subject) (e.g., a human patient))) a condition associated with protein misfolding, aggregation, incorrect clearance and function with one or more compounds of the present invention (e.g., any of the compounds capable of HSF activation described by Formulas I-XII).

The present invention is not limited to a particular method for treating a condition associated with protein misfolding, aggregation, incorrect clearance and function. In some embodiments, the methods comprise administering to a patient (e.g., human being or other mammal), in need thereof, one or more compounds of the present invention capable of facilitating HSF (e.g., HSF1) activation (e.g., any of the compounds described by Formulas I-XII) to improve intracellular quality control.

The methods are not limited to treating a particular condition benefiting from enhanced HSF (e.g., HSF1) activity. In a first embodiment of this aspect, conditions benefiting from HSF (e.g., HSF1) activity include, but are not limited to, Alzheimer's disease, Parkinson's disease, Huntington disease, Amyotrophic Lateral Sclerosis, a prion-based disease, hearing loss, tinnitus, hair loss associated with chemotherapy, cancer, cardiovascular conditions, including but not limited to congestive heart failure, macular degeneration, aging, wound healing, immune diseases and type 2 diabetes mellitus. In a second embodiment, the composition is co-administered with one or more therapeutic agents (e.g., anticonvulsant agents, antipsychotic agents, rauwolfia alkaloids, antidepressants, dopamine prodrugs, dopamine agonists, catechol-O-methyltransferase (COMT) inhibitors, anticholinergics, MAO-B inhibitors, N-methyl-D-aspartic acid inhibitors, AChE inhibitors, NMDA antagonists, free-radical scavengers, glutamate pathway antagonists, antispastic agents, Congo red and its analogs, anthracyclines, amphotericin B and its analogs, sulfated polyanions, tetrapyrroles, sulfonylurea agents, meglitinides, biguanides, thiazolidinediones, dipeptidyl peptidase IV (DPP-4) inhibitors, incretin mimetics, amylin analogs, and alpha-glucosidase inhibitors).

In certain embodiments, the present invention provides methods for identifying HSF1 activating agents. The present invention is not limited to a particular method for identifying HSF1 activating agents. In some embodiments, the methods comprise a) providing a yeast yhsfΔ strain expressing human HSF, wherein the yhsfΔ strain comprises a yeast HSF gene coupled with an inducible promoter (e.g., GAL promoter); b) growing the yhsfΔ strain on a medium having the inducer (e.g., galactose); c) exposing the yhsfΔ strain to a candidate compound; d) switching the yhsfΔ strain to a non-inducer growth medium; e) assessing the growth of the yhsfΔ strain; and f) characterizing the candidate compound as a HSF1 activating agent if the yhsfΔ strain grows on the non-inducer medium. In some embodiments, the human HSF is expressed via a pRS424-GPD-hHSF1 plasmid. In some embodiments, the non-inducer medium is a glucose medium.

In certain embodiments, the present invention provides pharmaceutical formulations containing one or more compounds of the present invention (e.g., any of the compounds capable of HSF activation described by Formulas I-XII). In some embodiments, such pharmaceutical formulations are used within methods for treating a particular condition benefiting from enhanced HSF (e.g., HSF1) activity.

Additional embodiments of the invention are set forth in the description which follows, or may be learned by practice of the invention.

DEFINITIONS

Figure 1:
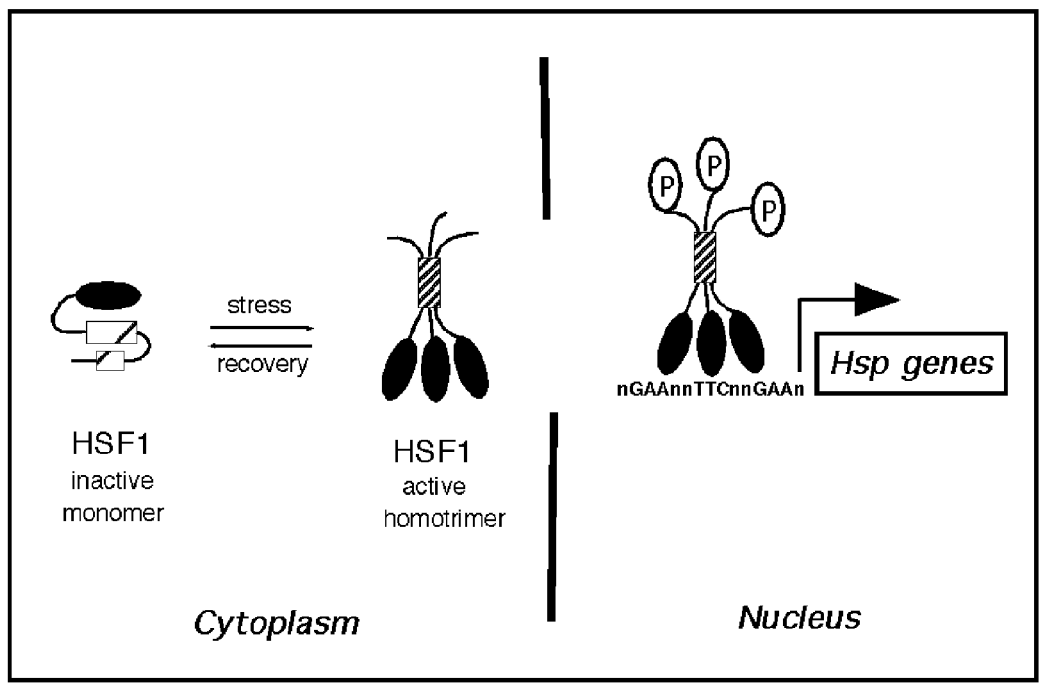
FIG. 1 shows a model for the activation of human HSF1. HSF1 is shown as an inactive monomer in the cytoplasm in the absence of stress. Stress conditions such as heat or unfolded proteins trigger HSF1 conversion to the DNA binding-active homo-trimer.

Unless noted otherwise, the chemical, biological, pharmacological, and other technical terms used herein are consistent with the uses of these terms in contemporary technical journals, patents, textbooks, and other references devoted to the appropriate art. For example, definitions and explanations of organic chemistry terms may be found in standard text such as the latest edition of *March's Advanced Organic Chemistry*, John Wiley & Sons, Inc, New York. (e.g. 5th Ed., 2001). In the interest of clarity and the convenience of the reader, the definitions of some terms frequently used herein are listed below.

"Alkyl" refers to a branched or straight chain hydrocarbon group derived by the removal of one hydrogen atom from a single carbon atom of a parent alkane, alkene or alkyne group. The term "saturated alkyl" is intended to include groups having exclusively single carbon-carbon bonds. The term "unsaturated alkyl" is specifically intended to include groups having any degree or level of unsaturation, i.e., groups having one or more double carbon-carbon bonds, groups having one or more triple carbon-carbon bonds and groups having mixtures of single, double and triple carbon-carbon bonds.

"Aryl" refers to an organic group derived from an aromatic hydrocarbon by removal of one hydrogen. Aryl encompasses: an aromatic ring, for example, benzene; bicyclic ring systems wherein at least one ring is an aromatic, for example, naphthalene and indane, and tricyclic ring systems wherein at least one ring is aromatic, for example, fluorene.

"Bicyclic" includes spirocyclic, ortho-fused and bridged bicyclic systems.

"Spirocyclic" refers to a pair of rings having a single atom in common.

"Ortho-fused" refers to a pair of rings having two adjacent atoms in common.

"Bridged bicyclic" refers to a pair of rings having at least three adjacent atoms in common.

"Chelate" refers to the chemical entity formed by the coordination of a compound to a metal ion at two (or more) points.

"Cycloalkyl" refers to a non-aromatic, monocyclic, bicyclic, or polycyclic ring comprising carbon and hydrogen atoms. A cycloalkyl group can have one or more carbon-carbon double or triple bonds in the ring so long as the ring is not rendered aromatic by their presence. The term "saturated cycloalkyl" is intended to include cyclic rings having exclusively single carbon-carbon bonds. The term "unsaturated cycloalkyl" is specifically intended to include cyclic rings having any degree or level of unsaturation, i.e., groups having one or more double carbon-carbon bonds, groups having one or more triple carbon-carbon bonds and groups having mixtures of single, double and triple carbon-carbon bonds.

"Disease" and/or "condition" refers to any disease, disorder, condition, symptom, or indication that is not a normal body function.

"Extended release" refers to dosage forms that provide for the delayed, slowed, over a period of time, continuous, discontinuous, or sustained release of the chemical entities of the present disclosure.

"Halogen" refers to a fluoro, chloro, bromo, or iodo group.

"Heteroaryl" means a monocyclic, bicyclic, or polycyclic aromatic ring comprising carbon and hydrogen atoms, and one or more heteroatoms, preferably, 1 to 3 heteroatoms chosen from N, O, and S.

"Heterocycloalkyl" refers to a non-aromatic monocyclic, bicyclic, or polycyclic ring comprising carbon and hydrogen atoms and at least one heteroatom, preferably, 1 to 3 heteroatoms selected from nitrogen, oxygen, and sulfur. A heterocycloalkyl group can have one or more carbon-carbon double bonds or carbon-carbon triple bonds, or carbon-heteroatoms double bonds in the ring as long as the ring is not rendered aromatic by their presence. The term "saturated heterocycloalkyl" is intended to include heterocyclic rings having exclusively single bonds in the ring. The term "unsaturated heterocycloalkyl" is specifically intended to include heterocyclic rings having any degree or level of unsaturation, i.e., groups having one or more double bonds, groups having one or more triple bonds and groups having mixtures of single, double and triple bonds.

"Leaving group" refers to an atom or a group capable of being displaced by a nucleophile and includes halogen, such as chloro, bromo, fluoro, and iodo, aryloxy, acetoxy, mesyloxy, tosyloxy, methoxy, trifluoromethanesulfonyloxy, and the like.

"Optionally" means that the subsequently described event or circumstance may or may not occur, and that the description includes instances where the event or circumstance occurs and instances in which the event does not.

"Pharmaceutically acceptable" refers to approved or approvable by a regulatory agency of the Federal or a state government or listed in the U.S. Pharmacopeia or other generally recognized pharmacopeia for use in animals, and more particularly in humans.

"Pharmaceutically acceptable excipient, carrier or adjuvant" refers to an excipient, carrier or adjuvant that can be administered to a subject, together with at least one chemical entity of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient or carrier.

"Pharmaceutical formulation," or synonymously "medicament," means a composition containing one or more pharmaceutically active compounds, e.g. one or more chemical entities of the present disclosure, and one or more pharmaceutically acceptable vehicles.

"Prodrug" refers to a derivative of a therapeutically effective compound that requires a transformation within the body to produce the therapeutically effective compound.

"Protecting group" refers to a grouping of atoms that when attached to a reactive group in a molecule masks, reduces or prevents that reactivity. Examples of protecting groups can be found in Green et. al., "Protective Groups in Organic Chemistry," (Wiley, $2^{nd}$ ed. 1991) and Harrison et. al., "Compendium of Synthetic Organic Methods," Vols. 1-8 (John Wiley and Sons, 1971-1996).

The term "salt" refers to a salt of a compound that is pharmaceutically acceptable and that possesses the desired pharmacological activity of the parent compound. Such salts includes but not limited to: salts formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, and the like. It is possible that a salt that is not pharmaceutically acceptable may be used as a chemical intermediate, but those situation will be note when and where they occur in these teachings.

"Solvate" refers to the compound formed by the interaction of a solvent and a compound. Suitable solvates are pharmaceutically acceptable solvates, such as hydrates, including monohydrates and hemi-hydrates.

"Stereoisomer" refers to an isomer that differs in the arrangement of the constituent atoms in space. Stereoisomers that are mirror images of each other and optically active are termed "enantiomers," and stereoisomers that are not minor images of one another are termed "diastereoisomers." A mixture of equal amounts of the two stereoisomers of an optically active substance, such as two enantiomers where such a mixture does not rotate plane-polarized light refers to as "racemic mixture".

"Subject" includes mammals, such as humans. The terms "patient," "human," and "subject" are used interchangeably and synonymously herein.

"Substituted" refers to a molecule in which one or more hydrogen atoms are replaced with one or more non-hydrogen atoms, functional groups or moieties.

"Therapeutically effective amount" refers to the amount of a compound that, when administered to a subject for treating a disease, or at least one of the clinical symptoms of a disease or disorder, is sufficient to affect such treatment for the disease, disorder, or symptom. An appropriate amount in any given instance can be readily apparent to those skilled in the art or capable of determination by routine experimentation.

"Treating," or "treatment" of, any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and inhibit at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder. In this context, the terms "a patient in need thereof," "a patient suffering from," or equivalent language means a patient that could benefit by the treatment being taught herein.

DETAILED DESCRIPTION

The proper synthesis, folding, trafficking, modifications, interactions, biochemical activities and eventual clearance of cellular proteins is essential for normal growth, development and maintenance during the life cycle of all organisms. Inappropriate folding, aggregation and accumulation of abnormal proteins is proteo-toxic to cells due to their dominant affects of insolubility, inappropriate interactions and long half-lives (see, e.g., Johnson, J, et. al., *Cell.* 1997 90(2), 201-204; Bukau, B, et. al., *Cell.* 2000 101(2), 119-122; Hartl, F, et. al., (1996) *Nature.* 1996 381, 571-580; Deuerling, E, et. al., *Crit. Rev. Biochem. Mol. Bio.* 2004 39, 261-277; Bukau, B., et. al., *Cell* 2006 125(3), 443-451; and Dickey, C, et. al., *Trends in Mol. Med.* 2007 13(1), 32-38).

Neuronal tissues and cells are exquisitely sensitive to defects in protein folding, aggregation and clearance and these defects are causally or correlatively associated with diseases that include Huntington's disease, Parkinson's disease, Alzheimer's disease, Amyotropic Lateral Sclerosis, prion diseases and other neurodegenerative disorders (see, e.g., Bonini, N. *Proc. Natl. Acad. Sci., USA,* 2002 99, 16407-16411; Muchowski, P, *Neuron* 2002 35, 9-12; Morimoto, R, *New England J. Med.* 2006 355, 2254-2255; Finkbeiner, S, et. al., *J. Neurosci.* 2006 26(41), 10349-10357; Furukawa, Y., et. al., *PNAS.* 2006 103(18), 7148-7153; Gidalevitz, T, et. al., *Science* 2006 311, 1471-1474). Many of these are diseases occur frequently in the elderly and result in a variety of symptoms due to loss of function of motor, dopaminergic and other neurons essential for a normal healthy life (see, e.g., Cummings, C. J. and Zoghbi, H, *Hum. Mol. Genet.* 2000 9, 909-916). Defects in protein folding, aggregation and clearance have also been implicated in type 2 diabetes mellitus (see, e.g., Chung, J, et. al. *PNAS* 2008 105(5), 1739-1744).

Several lines of evidence suggest that a familiar form of amyotrophic lateral sclerosis (ALS) is associated with the mis-folding and aggregation of mutated Cu/Zn superoxide dismutase (SOD1), one of the most abundant proteins in motor neurons (see, e.g. Prudencio, M, et. al., *Human Molecular Genetics.* 2009 Sep. 1, 18(17), 3217-26.). A second protein, ataxin-2 (Elden, et. al. *Nature* 2010 466, 1069-1075) showed that ataxin-2 intermediate-length polyglutamine expansions are associated with increased risk for ALS. Elevated levels of cellular proteins that carry out protein folding, protein chaperones, protect motor neurons from the toxic effects of misfolded SOD1. Given the great potential for a therapeutic role of elevated protein chaperone levels in ALS, small molecule elevation of the natural protein folding machinery in motor neurons is a promising avenue for the treatment of ALS.

Aging is associated with enhanced protein aggregation and generation of protein inclusions in virtually all cell types. Interestingly, several age-related neurodegenerative diseases like amyotrophic lateral sclerosis or Parkinson disease are directly associated with protein aggregation in distinct regions of the central nervous system despite the ubiquitous expression of affected proteins. Modification of the chaperon network can be beneficial for disease progression. See Kern, et al., "2010 HSF1-Controlled and Age-Associated Chaperone Capacity in Neurons and Muscle Cells of *C. elegans.*" *PLoS ONE* 5.

While many aspects of these complex processes of protein misfolding and aggregation are incompletely understood, a variety of individual protein chaperones and co-chaperone complexes function to fold, process, mature and degrade cellular proteins. (see, e.g., Johnson, J and Craig, E, 1997) *Cell.* 1997 90(2), 201-204; Bukau, B, et. al., *Cell.* 2000 101(2), 119-122; Hartl, F, *Nature* 1996 381, 571-580; Deuerling, E., and Bukau, B. (2004) *Crit. Rev. Biochem. Mol. Bio.* 2000 39, 261-277; Bukau, B., et. al., *Cell.* 2006 125 (3) 443-451; Dickey, C, et. al., *Trends in Mol. Med.* 2007 13(1), 32-38). Many neurodegenerative diseases are caused, for example, by genetically programmed changes in specific proteins, such as through the addition of poly glutamine (polyQ) coding sequences, by genetic defects in the protein folding and processing machinery, or by as yet poorly understood mechanisms by which abnormal protein conformations can be propagated in a protein-catalyzed fashion (see, e.g., Bonini, N, *Proc. Natl. Acad. Sci., USA.* 2002 99, 16407-16411; Muchowski, P, (2002) *Neuron.* 2002 35 9-12; Morimoto, R New England J. Med. 2006 355, 2254-2255; Finkbeiner, S, et. al., (2006) J. Neurosci. 2006 26 (41) 10349-10357; Furukawa, Y, et. al., PNAS 2006103(18), 7148-7153; Gidalevitz, T, et. al., Science 2006 311, 1471-1474; Cummings, C and Zoghbi, H Hum. Mol. Genet. 2000 9, 909-916).

Protein chaperones facilitate the folding, stabilization, solubilization and degradation of cellular proteins and are often included in the group of Heat Shock Proteins (Hsps) because their synthesis is elevated in response to heat and other stresses known to induce protein unfolding, aggregation and degradation (see, e.g., Morimoto, R. I., Tissieres, A., and Georgopoulos, C. (1994) *The Biology of Heat Shock Proteins and Molecular Chaperones*, Cold Springs Harbor Laboratory Press, Cold Springs Harbor N.Y. 1994; Lindquist, S. (1992) *Curr. Opinion in Genet. and Develop.* 1992 2, 748-755; Feige, U, et. al., (eds.) *Stress-inducible cellular responses*. Vol 77, Birkhauser, Verlag, Boston; Lindquist, S and Craig, E *Ann. Rev. Genet.* 1988 22, 631-677).

Protein chaperones act independently and in concert to ameliorate biochemical hallmarks or symptoms of the disease associated with unfolded or aggregated proteins. For example, in mammalian cell culture, mouse or *Drosophila* models of polyQ aggregation or alpha-synuclein toxicity, expression of the Hsp70 or Hsp40 chaperones can significantly suppress protein aggregation, increase protein solubility and turnover and ameliorate neuronal loss (see, e.g., Bailey, C, et. al., *Hum. Mol. Genet.* 2002 11(5), 515-523; Kitamura, A, et. al., *Nat. Cell Bio.* 2006 8(10), 1163-1170; Pavan, K., et. al., *Science.* 2002 295, 865-868; Chai, Y, et. al., *J. Neurosci.* 1999 19(23), 10338-10347; Muchowski, P, et. al., *Proc. Natl. Acad. Sci. USA.* 2000 97, 7841-7846; Jana, N, et. al., *Hum. Mol. Genet.* 2000 9, 2009-2018; Wyttenbach, A, et. al., (*Proc. Natl. Acad. Sci.* 2000 97, 2898-2903; Adachi, H, et. al., *J. Neurosci.* 2003 23, 2203-2211; Cummings, C, et. al., *Hum. Mol. Genet.* 2001 10, 1511-1518).

Additional studies suggest that Hsp70 and Hsp40 can synergize in the suppression of polyQ-mediated neuronal degeneration and that arimoclomal, an inducer of Hsp synthesis, significantly delays disease progression in a mouse model of ALS (see, e.g., Kieran, D, et. al., *Nature Medicine.* 200410, 402-405). From bacteria to human cells, Hsp synthesis is coordinately induced in response to stress conditions that result in protein unfolding, aggregation and proteolysis by stress-responsive transcription factors.

In cells from yeast to humans, the transcription of genes encoding Hsps is induced in response to stresses such as increased temperature through cis-acting promoter elements called Heat Shock Elements (HSEs), composed of variations of the inverted repeated pentameric consensus sequence 5"-nGAAnnTTCnnGAAn-3' (SEQ ID NO:01) (see, e.g., Morimoto, R et al., *The Biology of Heat Shock Proteins and Molecular Chaperones*, Cold Springs Harbor Laboratory Press, Cold Springs Harbor N.Y. 1994; Lindquist, S and Craig, E *Ann. Rev. Genet.* 1988 22, 631-677). In response to stress the Heat Shock Transcription Factor, HSF, binds as a homo-trimer to HSEs and activates target gene transcription. Indeed, HSFs and their cognate DNA binding site HSEs are two highly structurally and functionally conserved cis- and trans-acting regulatory factors. The baker's yeast *Saccharomyces cerevisiae* harbors a single gene encoding HSF that is essential for cell viability under all conditions tested. Recent genome-wide expression and chromatin-immuoprecipitation experiments demonstrate that yeast HSF directly activates a broad range of genes encoding proteins that function as chaperones, in protein turnover and a variety of additional stress protection roles (see, e.g., Hahn, J, et. al., *Molecular and Cellular Biology* 2004 24, 5249-5256).

In mammals, *Drosophila* and *C. elegans* HSF1 responds to stress to activate transcription of genes encoding a family of protein chaperones (Wu, C *Ann. Rev. Cell Dev. Biol.* 1995 11, 441-469; Pirkkala, L., Nykanen, et. al., *FASEB J.* 200115, 1118-1131; Hsu, A. L., (2003) *Science* 300: 1142-1145; Morley, J. F., and Morimoto, R. I. (2004) *Mol. Bio. Cell* 15: 657-664). While the precise mechanisms whereby HSF1 from humans and other organisms sense and respond to stress have not been elucidated, a model that summarizes current understanding of this process in human cells is shown in FIG. 1. HSF1 activation is a multi-step process that occurs post-translationally in response to elevated temperatures, the accumulation of unfolded proteins and other stressful conditions.

In the absence of acute stress, HSF1 is present largely in the cytoplasm as a monomer, and is thought to be associated with Hsp90, Hsp70 and other proteins (see, e.g., Zuo, et. al., *Cell.* 1998 94, 471-480; Ali, A, et. al., (1998) *Mol. Cell. Biol.* 199818, 4949-4960; Guo, Y., et. al., *J. Biol. Chem.* 2001 276, 45791-45799). In vitro and in vivo experiments suggest that HSF1 is retained in the momomeric state through intramolecular interactions between two coiledcoil regions, Leucine Zipper 1-3 (LZ1-3) and Leucine Zipper 4 (LZ4) (see, e.g., Rabindran, S, et. al., *Science.* 1993 259, 230-234. Indeed, point mutations in Leucine Zipper 4 (HSF11z4m) cause constitutive HSF1 homo-trimerization in mammalian cells. In response to stress, HSF1 is converted to a homo-trimer that is stabilized by inter-molecular coiledcoil interactions and accumulates in the nucleus, where it engages in high affinity binding to HSEs within target gene promoters and activates target gene transcription. Hsp target gene activation by HSF1 is transient, and correspondingly, HSF1 is ultimately converted back to the low affinity DNA binding monomeric form in the cytosol. HSF1 is phosphorylated both under basal conditions where this modification is thought to maintain the protein in an inactive state and in response to stress, with this latter modification having functional consequences that are not well understood.

Some small molecule activators of HSF1 function through the inhibition of the Hsp90 chaperone complex. The molecules described in this application, and discovered with this technology, do not interact with, nor inhibit Hsp90. Previous studies suggest that Hsp90 and additional cochaperones exist in a heteroprotein complex that, in addition to their central role in cellular signaling, function to repress HSF1 in the absence of stress. In response to proteotoxic stress or pharmacological inhibitors of Hsp90, this complex dissociates, resulting in the multimerization of HSF1 Zou, J, et. al., *Cell,* 1998 94, 471-180. As such, we reasoned that the inability of human HSF1 to be activated in yeast might stem from a repressive interaction between yeast Hsp90 and human HSF1 and that HSF1A promotes HSF1 activation in yeast by disrupting this interaction.

To test this hypothesis, the efficacy of the potent Hsp90 inhibitors geldanamycin and radicicol, in promoting human HSF1-dependent yeast growth was evaluated. Exposure to either 10 mM geldanamycin or 10 mM radicicol for 3 h activated expression of the yeast HSF-dependent SSA3-lacZ reporter gene, reflective of their previously established function as Hsp90 inhibitors in yeast Hahn, J. S. et. al., (2004) *Mol Cell BIol* 24:5249-5256. However, neither geldanamycin nor radicicol were able to promote human HSF1-dependent yeast growth under the same conditions in which they are potent Hsp90 inhibitors, suggesting that HSF1A is unlikely to act as an Hsp90 inhibitor. Consistent with this notion, HSF1 was not activated in a yeast strain that expresses, 5% of the wild-type levels of Hsp90 Yam, A, et. al., *Nat Struct, Mol. Biol.* 2008 15, 1255-1262.

Many pharmacological inhibitors of Hsp90 such as geldanamycin and 17-AAG target the amino-terminal ATP binding pocket of Hsp90, thereby inhibiting its chaperone function. To test whether HSF1A has affinity for the Hsp90 ATP-binding pocket, we performed competitive binding assays in vitro using a biotinylated geldanamycin (GD-B) molecule. The high-affinity Hsp90 inhibitor 17-AAG was able to compete with GD-B for Hsp90 binding at 1 mM and 10 mM. In contrast, HSF1A, even at concentrations 100-fold higher than GD-B, was unable to compete for Hsp90 binding suggesting that HSF1A does not bind the ATP-binding pocket of Hsp90. Because other small molecule inhibitors of Hsp90, including celastrol, novobiocin, and EGCG, are thought to bind Hsp90 at the carboxy-terminus Amolins, M and Blagg, B, *Mini Rev Med. Chem.* 2009 9, 140-152, we ascertained whether HSF1A could bind to Hsp90 at a region outside of the ATPbinding pocket. To assay for HSF1A binding to Hsp90, we generated an HSF1A-biotin conjugate (HSF1A-B)) and assayed the ability of HSF1A-B to interact with Hsp90. Although GD-B readily interacted with Hsp90 HSF1A-B, assayed at a concentration 10-fold higher than GD-B, did not interact with Hsp90. Furthermore, HSF1A-B did not interact with Hsp90 or the cochaperones Cdc37, Hop, p23, or Hsp70, nor HSF1 itself in pull-down experiments with mammalian cell extracts (unpublished data). Given that geldanamycin and radicicol cannot promote human HSF1-dependent yeast growth and that HSF1A does not interact with Hsp90, together these data strongly suggest that HSF1A is not acting as an Hsp90 inhibitor in activating HSF1 in yeast or mammalian cells (Neef, D et. al., *Plos Biology.* 2010 8: e1000291)

Accordingly, the present invention provides small molecules (e.g., compounds) capable of activating heat shock factors (e.g., facilitating HSF1 homo-trimerization), activating heat shock factor (e.g., HSF1) target gene expression (e.g., Heat Shock Elements) and protein expression (e.g., Heat Shock Proteins), methods for their discovery, and their therapeutic and/or research uses. Exemplary compositions and methods of the present invention are described in more detail in the following sections: I. HSF Activating Compound Screens; II. HSF Activating Compounds; III. Pharmaceutical Compositions; and IV. Therapeutic Applications.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et. al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et. al., eds., 1987, and periodic updates); "PCR: the polymerase chain reaction" (Mullis et. al., eds., 1994); and "Current protocols in immunology" (J. E. Coligan et. al., eds., 1991), each of which is herein incorporated by reference in its entirety.

I. HSF Activating Compound Screens

In some embodiments, the present invention provides screens for identifying activators of heat shock factor (e.g., activators capable of facilitating HSF1 homo-trimerization), and for identifying activators of heat shock factor (e.g., HSF1) target gene expression (e.g., Heat Shock Elements) and protein expression (e.g., Heat Shock Proteins). The screen is not limited to identifying activators of a particular heat shock factor. In some embodiments, the screens identify HSF1 activators, HSF2 activators, and/or HSF4 activators. The present invention is not limited to identifying a particular type of heat shock factor activator.

The present invention is not limited to a particular type of screen for identifying heat shock factor (e.g., HSF1) activators. In some embodiments, the present invention provides a yeast based screen. The present invention is not limited to use of a particular type of yeast. In some embodiments, the screen comprises genetically modified yeast. The screen is not limited to a particular type of genetically modified yeast. In some embodiments, the screens provide yeast that are genetically modified such that expression of yeast HSF is regulated. In some embodiments, the screens provide yeast that are genetically modified such that the yeast express human HSF1. While human HSF1 and yeast HSF have similar structures, bind as homo-trimers to conserved HSEs and activate functionally common Hsp genes, expression of wild type human HSF1 cannot suppress the viability defect associated with yeast HSF deletion (yhsfΔ) cells (see, e.g., Liu, X. D., et. al., (1997) *EMBO J.* 16, 6466-6477). Biochemical analysis of human HSF1 demonstrated that human HSF1 exists in yeast as a monomer and is not able to homo-trimerize under basal or stress conditions. Indeed, expression in yhsfΔ cells of the human HSF11z4m mutant, which is constitutively trimerized in culturized human cells, is able to rescue the yhsfΔ viability defect, bind to and activate stress-inducible target gene transcription such as from the yeast Hsp70 gene, and exist as a homo-trimer in yeast.

The present invention is not limited to any mechanism of action. Indeed, an understanding of the mechanism is not necessary to practice the present invention. Nonetheless, it is contemplated that human HSF1 fails to function in yeast due to a homotrimerization inability. In some embodiments, the screens of the present invention identify activators (e.g., compounds) capable of facilitating homotrimerization of HSF1.

The screens are not limited to a particular manner of genetically modifying yeast HSF expression. In some embodiments, genetically modified yeast HSF expression occurs through deleting the HSF gene open reading frame and 5' and 3' regions, thereby rendering a yhsfΔ strain that is inviable. In some embodiments, the yhsfΔ strains have a yeast HSF gene coupled with an inducible promoter (e.g., GAL1-10) thereby rendering growth of such yhsfΔ strains viable on a selectable medium (e.g., galactose). In some embodiments wherein yhsfΔ strains express a yeast HSF gene coupled with an GAL promoter, the strain is inviable at any temperature or under any condition tested when cells are shifted to a glucose medium thereby extinguishing yeast HSF expression. In some embodiments, the yhsfΔ strains expressing a yeast HSF gene coupled with a selectable promoter additionally harbor a plasmid configured for human HSF1 (hHSF1) expression. In some embodiments, the plasmid configured for expression of hHSF is pRS424-GPD-hHSF1 (wherein GPD is the constitutively expressed glucose phosphate dehydrogenase promoter).

Figure 2:
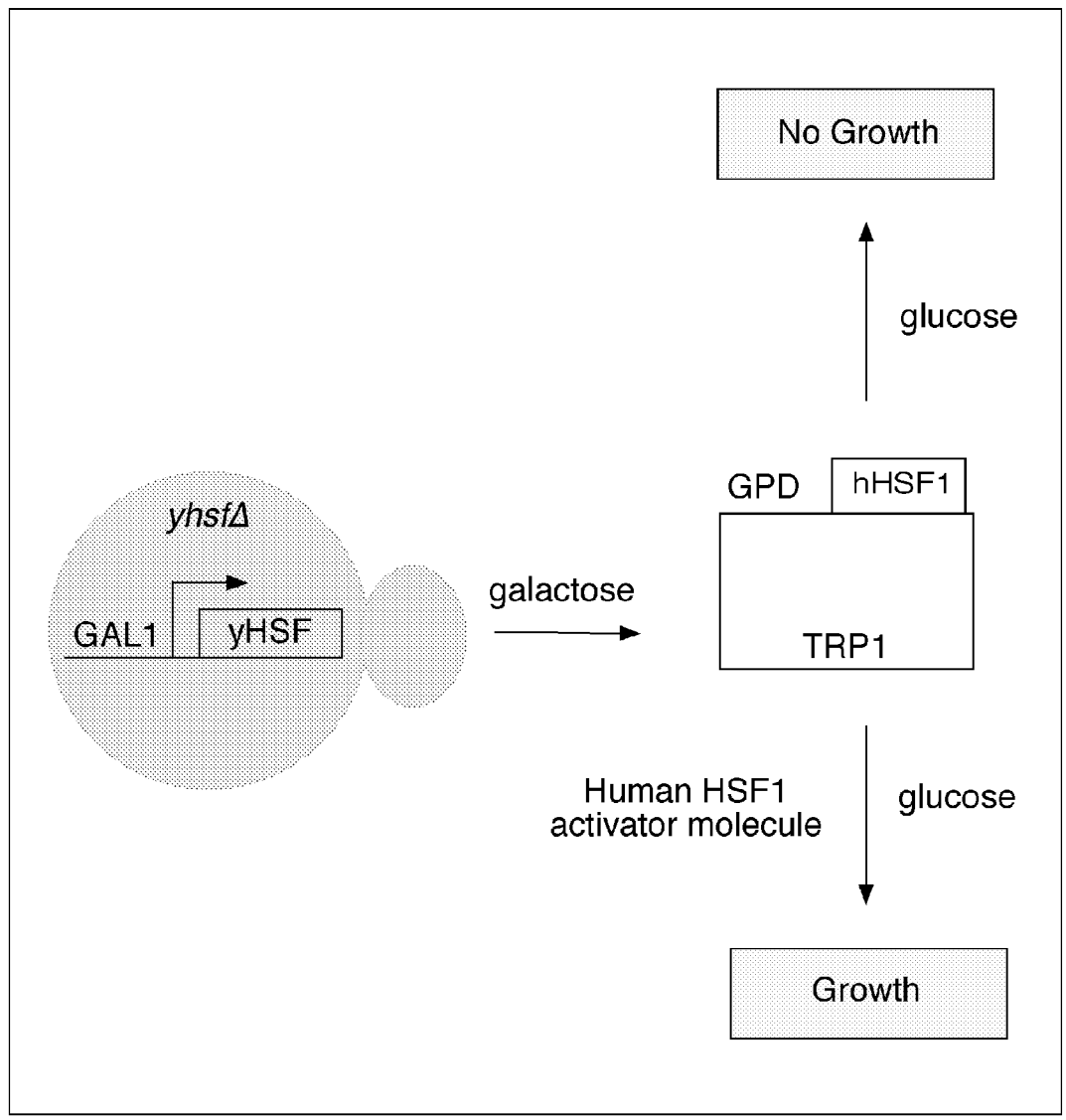
FIG. 2 shows yeast-based screen for small molecule activators of human HSF1 (hHSF1). Cells harboring the hHSF expression plasmid and grown on glucose to extinguish yeast HSF (yHSF) expression do not grow. Small molecules able to activate hHSF1 allow growth on glucose.

In some embodiments, as shown in FIG. 2, the yhsfΔ strains expressing a yeast HSF gene coupled with a selectable promoter configured for expression hHSF are used for identifying activators of hHSF1 (e.g., activators capable of facilitating HSF1 homotrimerization), identifying activators of HSF1 target gene expression (e.g., Heat Shock Elements), identifying activators of HSF1 protein expression (e.g., Heat Shock Proteins), and/or activation of protein chaperone activity (e.g., increased protein folding, increased protein solubilization, protein degradation). This screen has several features, including but not limited to, (1) when yeast HSF expression is extinguished, only cells in which human HSF1 has been activated are viable, providing a screen with a very low background; (2) this strain allows for positive selection of human HSF1 activator molecules; (3) this strain in conjunction with an additional strain lacking hHSF1 expression permits identification of molecules that act exclusively in a human HSF1-dependent manner rather than via the prevention of yeast HSF repression by glucose or yeast; and (4) the screen is amenable to automated liquid handling and optical density determination and is therefore high throughput in nature.

The screens are not limited to a particular method for identifying activators of hHSF1. In some embodiments, for example, a yhsfΔ strain expressing hHSF1 is exposed to a small molecule under conditions inviable for growth absent homotrimerization of the hHSF1. Growth in such conditions indicates that the small molecule is an activator of hHSF1 (see, FIG. 2). A lack of growth indicates that the small molecule is not an activator of hHSF1 (see, FIG. 2).

In some embodiments, the yeast strains used in the screens are genetically modified to maximize small molecule accumulation. The yeast strains are not limited to a particular manner of genetic modification to maximize small molecule accumulation. In some embodiments, genetic modification to maximize small molecule accumulation is accomplished through, for example, sequential deletion of the PDR5, SNQ2 and ERG6 genes in the yhsfΔ background. PDR5 and SNQ2 encode ATP binding cassette integral plasma membrane transport proteins which mediate multidrug resistance by exporting compounds with a broad range of structures and relatively low specificity (see, e.g., Emter, R, *FEBS Letters*. 2002 521, 57-61). As such, yeast cells lacking Pdr5 and Snq2 accumulate organic molecules to a significantly higher steady state level than wild type strains. The ERG6 gene, encoding delta(24)-sterol C-methyltransferase, is a key enzyme in ergosterol biosynthesis. Erg6 mutants exhibit enhanced diffusion rates of lipophilic molecules across the plasma membrane (see, e.g., Emter, R, *FEBS Letters* 2002 521, 57-61). In some embodiments, yeast strains having sequential deletion of PDR5, SNQ2 and ERG6 genes in the yhsfΔ background hyper-accumulate organic compounds.

II. HSF Activating Compounds

Experiments conducted during the course of development of embodiments for the present invention identified HSF activating compounds (e.g., compounds capable of facilitating HSF1 homotrimerization, compounds capable of activating HSF1 target gene expression (e.g., Heat Shock Elements), compounds capable of activating HSF1 protein expression (e.g., Heat Shock Proteins), compounds capable of activating protein chaperone activity (e.g., increased protein folding, increased protein solubilization, protein degradation). An understanding of the mechanism by which the compounds activate HSF proteins is not required to practice the present invention.

Accordingly, the present invention provides compounds capable of activating HSF proteins. The present invention is not limited to particular compounds capable of activating HSF proteins. Examples include, but are not limited to, any of the compounds described within Formulas I-XII.

III. Pharmaceutical Compositions, Formulations, and Exemplary Administration Routes and Dosing Considerations Exemplary embodiments of various contemplated medicaments and pharmaceutical compositions are provided below.

A. Preparing Pharmaceutical Formulations

Compounds of the present invention are useful in the preparation of pharmaceutical formulation, also synonymously referred to herein as "medicaments," to treat a variety of conditions associated with protein misfolding and/or reduced chaperone activity. In addition, the compounds are also useful for preparing medicaments for treating other disorders wherein the effectiveness of the compounds are known or predicted. Such disorders include, but are not limited to, neurological disorders. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such pharmaceutical formulations can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate. Likewise, those for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent. It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In some embodiments, the compounds of the present invention are provided in unsolvated form or are in non-aqueous solutions (e.g., ethanol). The compounds may be generated to allow such formulations through the production of specific crystalline polymorphs compatible with the formulations.

In certain embodiments, the present invention provides instructions for administering said compound to a subject. In certain embodiments, the present invention provides instructions for using the compositions contained in a kit for the treatment of conditions characterized by the dysregulation of apoptotic processes in a cell or tissue (e.g., providing dosing, route of administration, decision trees for treating physicians for correlating patient-specific characteristics with therapeutic courses of action). In certain embodiments, the present invention provides instructions for using the compositions contained in the kit to treat a variety of medical conditions associated with irregular HSF1 activity (e.g., medical conditions involving irregular HSF1 activity) (e.g., medical conditions involving irregular chaperone activity) (e.g., Alzheimer's disease, Parkinson's disease, Huntington's disease, Amyotrophic Lateral Sclerosis, prion-based diseases, type 1 diabetes mellitus, type 2 diabetes mellitus).

C. Exemplary Administration Routes and Dosing Considerations

Various delivery systems are known and can be used to administer therapeutic agents (e.g., exemplary compounds as described in Section III above) of the present invention, e.g., encapsulation in liposomes, microparticles, microcapsules, receptor-mediated endocytosis, and the like. Methods of delivery include, but are not limited to, intra-arterial, intramuscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

It is contemplated that the agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is a neurological disorder (e.g., Huntington Disease), the additional agent can be an anticonvulsant medication. The additional agents to be co-administered can be any of the well-known agents in the art for a particular disorder, including, but not limited to, those that are currently in clinical use and/or experimental use.

IV. Therapeutic Application

In certain embodiments, the present invention provides methods (e.g., therapeutic applications) for treating conditions associated with protein misfolding. The present invention is not limited to a particular type of method. In some embodiments, the methods for treating conditions associated with protein misfolding comprise a) providing: i. target cells having misfolded proteins; and ii. a composition (e.g., a composition comprising exemplary HSF1 activating compounds as described in Section III above); and b) exposing the target cells to the composition under conditions such that the exposure results in increased HSF1 activity. The methods are not limited to treating a particular condition associated with protein misfolding. In some embodiments, the condition associated with protein misfolding is a medical condition involving irregular chaperone activity. In some embodiments, the condition associated with protein misfolding is enhanced aging, Alzheimer's disease, Parkinson's disease, Huntington disease, Amyotrophic Lateral Sclerosis, and prion-based disease (e.g., transmissible spongiform encephalopathy, Bovine spongiform encephalopathy, Creutzfeldt-Jakob disease, and Kuru). In some embodiments, the condition associated with protein misfolding is type 2 diabetes mellitus (see, e.g., Chung, J, et. al., *PNAS* 2008, 1739-1744). The methods are not limited to a particular type of target cells. In some embodiments, the target cells are neurological cells. In some embodiments, the target cells are within a living mammal (e.g., human, horse, dog, cat, pig, rat, mouse, ape, monkey).

Additionally, any one or more of these compounds can be used in combination with at least one other therapeutic agent (e.g., potassium channel openers, calcium channel blockers, sodium hydrogen exchanger inhibitors, anticonvulsant agents, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, anti-spastic agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents selected from ACE inhibitors, AT-1 receptor antagonists, ET receptor antagonists, dual ET/AII receptor antagonists, and vasopepsidase inhibitors, or an antiplatelet agent selected from GPIIb/IIIa blockers, $P2Y_1$ and $P2Y_{12}$ antagonists, thromboxane receptor antagonists, and aspirin) in along with a pharmaceutically-acceptable carrier or diluent in a pharmaceutical composition. Additional therapeutic agents for Huntington disease include, but are not limited to, anticonvulsant agents (e.g., valproic acid, clonazepam), antipsychotic agents (e.g., risperidone, haloperidol), rauwolfia alkaloids (e.g., reserpine), antidepressants (e.g., proxetine). Additional therapeutic agents for Parkinson's disease include, but are not limited to, dopamine prodrugs (e.g., levodopa/carbidopa), dopamine agonists (e.g., apomorphine, bromocriptine, pergolide, pramipexole, ropinirole, rotigotine), catechol-O-methyltransferase (COMT) inhibitors (e.g., tolcapone, entacapone, levodopa, carbidopa, entacapone), anticholinergics (e.g., trihexyphenidyl, benztropine mesylate), MAO-B inhibitors (e.g., selegiline, rasagiline), and N-methyl-D-aspartic acid inhibitors (e.g., amantadine). Additional therapeutic agents for Alzheimer's disease include, but are not limited to, centrally acting AChE inhibitors (e.g., rivastigmine), NMDA antagonists (e.g., memantine), and free-radical scavengers (e.g., tocopherol). Additional therapeutic agents for Amyotrophic Lateral Sclerosis include, but are not limited to, glutamate pathway antagonists (e.g., riluzole), antispastic agents (e.g., baclofen). Additional therapeutic agents for prion diseases include, but are not limited to, Congo red and its analogs, anthracyclines, amphotericin B and its analogs, sulfated polyanions, and tetrapyrroles. Additional therapeutic agents for type 2 diabetes mellitus include, but are not limited to, sulfonylurea agents (e.g., glipizide, glyburide, glimepiride), meglitinides (e.g., repaglinide, nateglinide), biguanides (e.g., metformin), thiazolidinediones (e.g., pioglitazone, rosiglitazone), dipeptidyl peptidase IV (DPP-4) inhibitors (e.g., sitagliptin), incretin mimetics (e.g., exenatide), amylin analogs (e.g., pramlintide acetate), and alpha-glucosidase inhibitors (e.g., acarbose, miglitol).

EXPERIMENTAL

The following examples are provided to demonstrate and further illustrate certain preferred embodiments of the present invention and are not to be construed as limiting the scope thereof.

Example I

This example describes synthetic procedures for the compounds of the present invention. The compounds of the present invention (e.g., compounds capable of HSF activation) can be prepared by methods well known in the art from readily available starting materials using the following general methods and procedures. The skilled artisan will appreciate that where typical or preferred process conditions, such as, reaction temperatures, times, mole ratios of reactants, solvents, pressures, are given, other process conditions can also be used unless otherwise stated. Reaction conditions may vary with the reactants or solvent used, but such conditions can be determined by one skilled in the art by routine optimization procedures.

Furthermore, the compounds of the present invention (e.g., compounds capable of HSF activation) can contain one or more chiral centers. Accordingly, if desired, such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure, unless otherwise indicated. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

Additionally, as will be apparent to those skilled in the art, conventional protecting groups may be necessary to prevent certain functional groups from undergoing undesired reactions. Suitable protecting groups for various functional groups as well as suitable reaction conditions for protection and deprotection of certain functional groups are well known in the art. For example, the protecting groups which are described in T. W. Greene and P. G. Wuts, *Protecting Groups in Organic Synthesis*, Third Edition, Wiley, New York, 1999, and references cited therein.

The compounds of the present invention (e.g., compounds capable of HSF activation) can be isolated and purified by techniques well known in the art, such as extraction, evaporation, distillation, trituration, chromatography, and recrystallization. General synthetic schemes to prepare the compounds of the present disclosure are presented in the reaction schemes provided herein.

A compound of Formula II can be prepared as illustrated in Scheme 1. A General method for the synthesis of substituted pyrazole-carboxamides and pyrazole-sulfonamides can be found in Regan, J.; et. al. *J. Med. Chem.* 2002, 45, 2994-3008, Bagley, M.; et. al. *Org. Biomol. Chem.* 2006, 4, 4158-4164, Ohta, H.; et. al. *Bioorg. Med. Chem.* 2008, 16, 1111-1124, and references cited therein.

Preparation of substituted 5-amino-pyrazolyl intermediate 3 can be achieved by treating an appropriately substituted hydrazine 1 with a substituted acetonitrile 2 under cyclization reaction conditions (e.g., microwave reaction conditions). Treatment of intermediate 3 with a sulfonic acid derivative, $R^8S(O)_2X$, where X is a leaving group such as Cl, can afford the pyrazole-sulfonamide compounds 4. In addition, amide formation of the appropriately substituted 5-amino-pyrazolyl intermediate 3 after treatment with an acyl derivative, $R^9COX$, where X is a leaving group such as Cl, OH, OMe, or OEt, can provide the pyrazole-carboxamide compound 5. Certain starting materials 1 and 2 are commercially available or can be prepared by methods of the art.

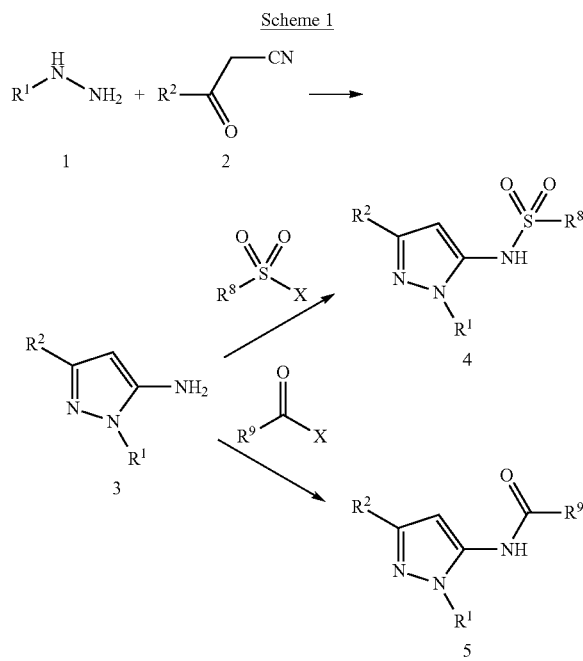

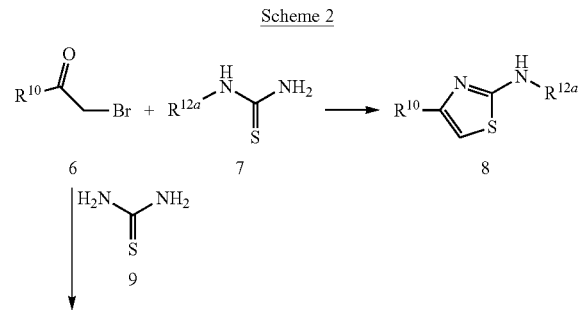

A compound of Formula IV can be prepared as illustrated in Scheme 2. A General method for the synthesis of N-substituted thiazole compounds can be found in Bramley, S. E.; et. al. *J. Chem. Soc. Perkin Trans.* 1 1987, 639-643, Bursavich, M. G.; et. al. *Bioorg. Med. Chem. Lett.* 2010, 20, 1677-1679, and references cited therein.

Treatment of a substituted bromo-ketone 6 with a substituted thiourea 7 under cyclization reaction conditions can provide the corresponding N-substituted thiazole compound 8. Preparation of thiazole-carboxamide substituted compounds II can be achieved by treating an appropriately substituted bromo-ketone 6 with thiourea 9 under cyclization reaction conditions to provide the corresponding 2-amino-thiazole intermediate 10. Amide formation can be achieved after treatment of the appropriately substituted 2-amino-thiazole intermediate 10 with an acyl derivative, R⁹COX, where X is a leaving group such as Cl, OH, OMe, or OEt, to provide the thiazole-carboxamide compound 11. Certain starting materials 6 and 7 are commercially available or can be prepared by methods known to those skilled in the art.

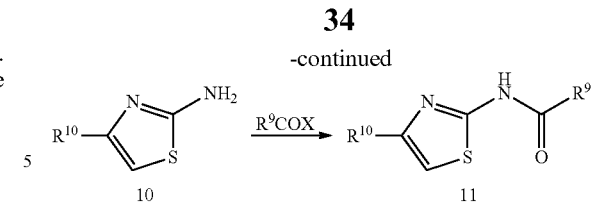

A compound of Formula V can be prepared as illustrated in Schemes 3 and 4. A General method for the synthesis of N-substituted bicyclic thiazole compounds can be found in Martin, R. E.; et. al. *Bioorg. Med. Chem. Lett.* 2009, 19, 6106-6113, and references cited therein.

Treatment of a cyclic thiazole derivative 12 (Scheme 3), where X is a leaving group such as Br, Cl, OMe, OMs, OTs or OEt with a substituted amine 13 can provide the N-substituted thiazole compound 14. Certain starting materials 12 and 13 are commercially available or can be prepared by methods known to those skilled in the art.

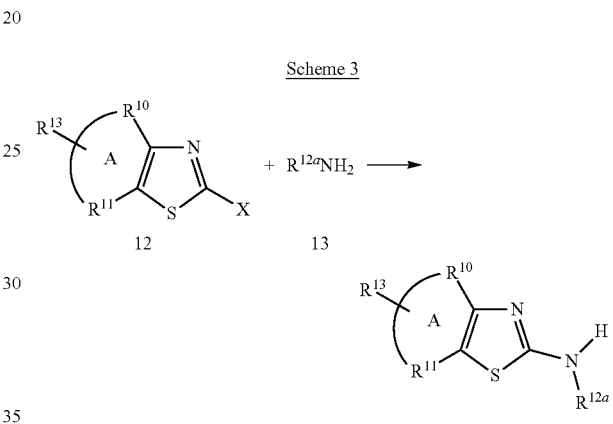

Alternatively, a compound of Formula V can be prepared as illustrated in Scheme 4. Treatment of a substituted cyclic bromo-ketone 15 with a substituted thiourea 16 under cyclization reaction conditions can provide the N-substituted thiazole compound 14. Likewise, treatment of an appropriately substituted cyclic bromo-ketone 15 with thiourea under cyclization reaction conditions can provide the corresponding 2-amino-thiazole cyclic intermediate 18. Amide formation of the appropriately substituted 2-amino-thiazole intermediate 18 with an acyl derivative, R⁹COX, where X is a leaving group such as Cl, OH, OMe, or OEt, can provide the thiazole-carboxamide compound 19. Certain starting materials 15 and 16 are commercially available or can be prepared by methods known to those skilled in the art.

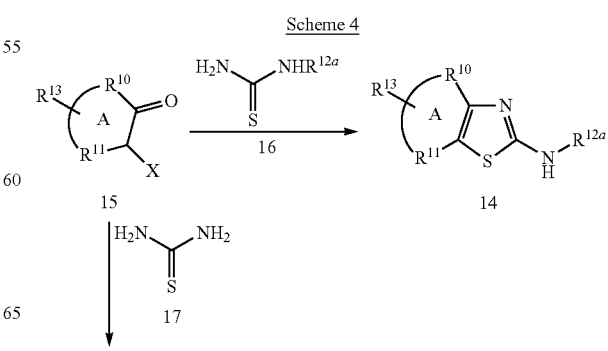

35

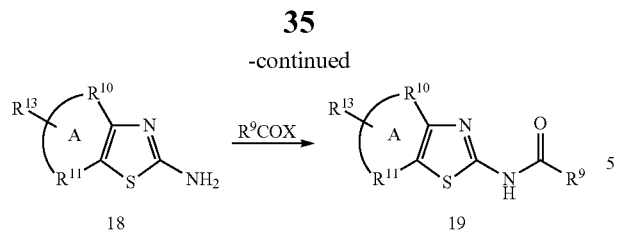

18    19

A compound of Formula VII can be prepared as illustrated in Scheme 5.

Reaction of the bromo-benzyl derivative 20 with an amine 21 provides the substituted amino-benzyl derivative 22. In turn, the NH functional group of compound 22 can be protected using a suitable protecting group reagent, e.g., Boc$_2$O, to afford the corresponding amino-protected intermediate 23. Amidation reaction of 23 with an amine 24 provides the benzamide compound 25. Reduction of the NO$_2$ group to the corresponding NH$_2$ group can be achieved with a reducing agent, e.g., SnCl$_2$. Removal of the N-protecting group followed by a carbonylation-cyclization reaction affords the final 1,2,3,4-tetrahydroquinazoline compound 28.

Scheme 5

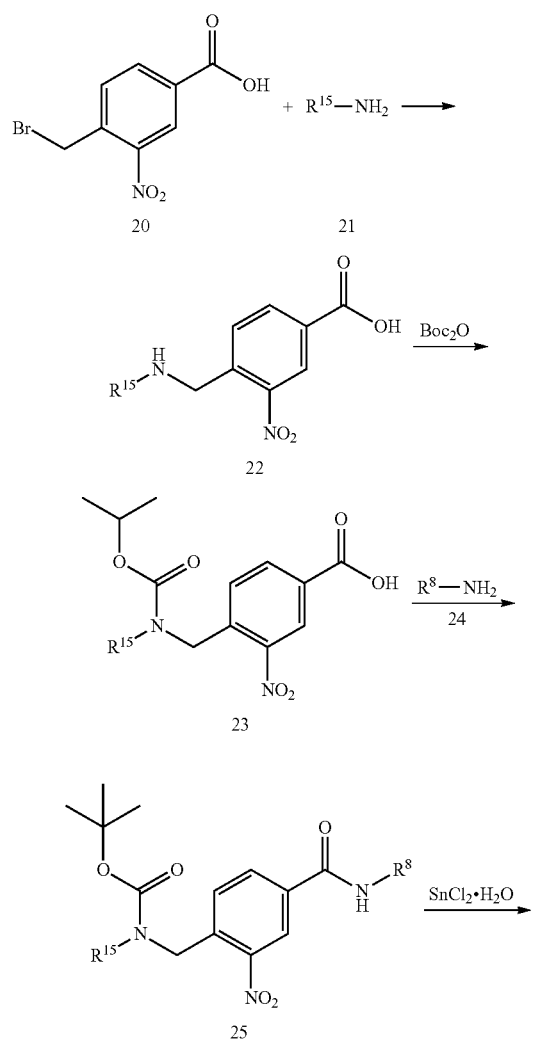

36

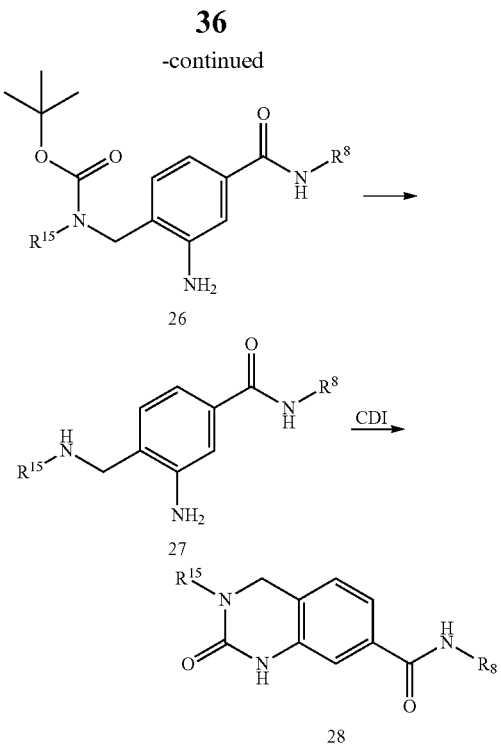

A compound of Formula IX can be prepared as illustrated in Scheme 6. A General method for the synthesis of 1,2,4-oxadiazoles can be found in Elzein, E.; et. al. *Bioorg. Med. Chem. Lett.* 2006, 16, 302-306, Liu, K.; et. al. *J. Med. Chem.* 2008, 51, 7843-7854, and references cited therein.

A substituted nitrile compound 29 can be treated with hydroxylamine to provide the N-substituted carboxamidine 30. Reaction of compound 30 with chloroacetyl chloride 31 can afford the chloro-methyl oxadiazolyl derivative 32, which in turn can be treated with a substituted amino compound 33 to afford the oxadiazolyl compound derivative 34.

Scheme 6

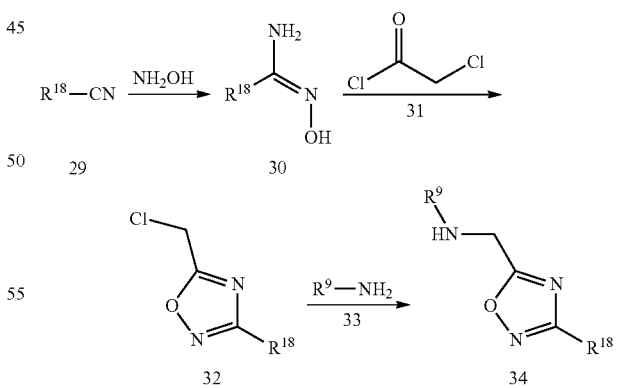

A compound of Formula XI can be prepared as illustrated in Scheme 7. Reaction of the bromo-phenyl ketone 35 with the diamine compound 36 provides the corresponding phenylethanone intermediate 37. Treatment of 37 with an amine 38 under reductive-amination reaction conditions provides the final phenylethane substituted-1,2-diamine compound 39.

Scheme 7

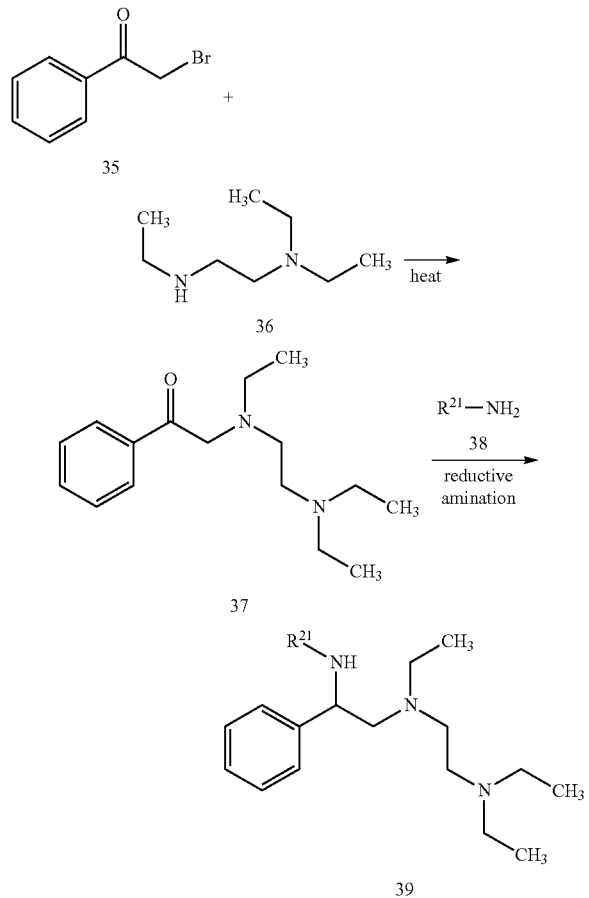

Example II

This example describes the synthesis of 4-Butyl-N-(3-phenyl-1-o-tolyl-1H-pyrazol-5-yl)benzamide.

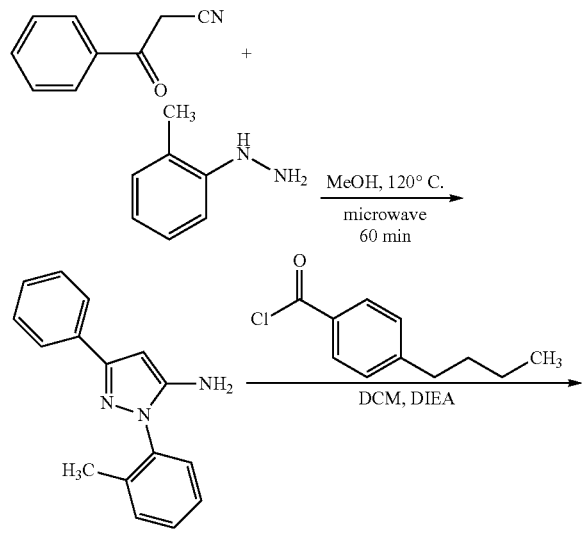

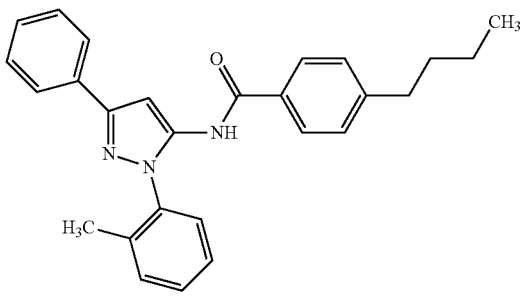

Benzoylacetonitrile (500 mg, 3.44 mmol) and o-tolylhydrazine hydrochloride (574 mg, 3.61 mmol) were placed in a microwave vial and dissolved in methanol (1.7 mL). The reaction vessel was sealed, placed in a microwave oven and heated at 120° C. for 1 hour. After this period, the reaction mixture was concentrated onto silica gel and purified by flash chromatography (0-50% ethyl acetate/hexanes gradient) to afford the desired intermediate, 5-phenyl-2-o-tolyl-2H-pyrazol-3-ylamine (392 mg). LC/MS: Calc. $C_{16}H_{15}N_3$ 249.13 amu; Obs. $[M+H]^+$=250.2 amu.

5-Phenyl-2-o-tolyl-2H-pyrazol-3-ylamine, compound prepared above, (75 mg, 0.30 mmol) was dissolved in dichloromethane (1 mL) and DIEA (105 µL, 0.600 mmol) followed by the addition of 4-n-butylbenzoyl chloride (63 mg, 0.33 mmol). The reaction was heated at 50° C. overnight. After this period, the reaction mixture was concentrated onto silica gel and purified by flash chromatography (0-50% ethyl acetate/hexanes gradient). The fractions were concentrated in vacuo and re-purified by reverse phase HPLC to afford the title compound (26 mg). LC/MS: Calc. $C_{27}H_{27}N_3O$ 409.21 amu; Obs. $[M+H]^+$=410.3.

Example III

This example describes the synthesis of 4-Ethyl-N-(1-phenyl-3-(thiophen-2-yl)-1H-pyrazol-5-yl)benzenesulfonamide.

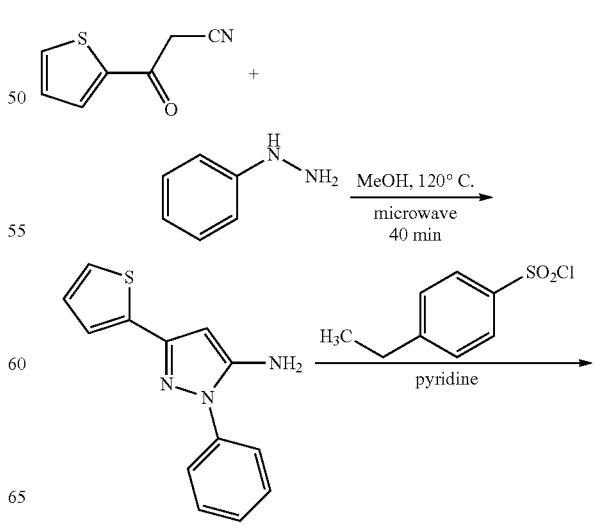

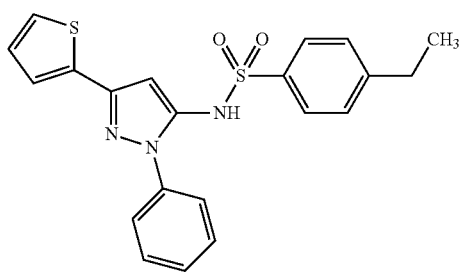

Phenyl hydrazine (143 mg, 1.32 mmol) and 3-oxo-3-(2-thienyl)propionitrile (200 mg, 1.32 mmol) were placed in a microwave vial and dissolved in methanol (660 μL). The vial was sealed, placed in a microwave oven and heated at 120° C. for 40 minutes. After this period, the reaction mixture was concentrated to dryness in vacuo. The residue was redissolved in ethyl acetate and the organic solution washed with water, saturated aqueous NaHCO$_3$ and brine, respectively. The organic layer was dried over anhydrous Na$_2$SO$_4$ and concentrated. The crude material was purified by flash chromatography (20-50% ethyl acetate/hexanes gradient) to afford the desired intermediate, 2-phenyl-5-thiophen-2-yl-2H-pyrazol-3-ylamine (315 mg).

Next, the 2-phenyl-5-thiophen-2-yl-2H-pyrazol-3-ylamine, compound obtained above, (315 mg, 1.30 mmol) was dissolved in pyridine (3 mL) and 4-ethylbenzene sulfonyl chloride (211 μL, 1.30 mmol) added to the reaction vessel. The reaction mixture was stirred at room temperature for 1 hour followed by heating at 60° C. for 16 hours. After this period, the reaction mixture was concentrated in vacuo and the residue was redissolved in ethyl acetate and the organic solution washed with water, saturated aqueous NaHCO$_3$ and brine, respectively. The organic layer was dried over anhydrous Na$_2$SO$_4$, concentrated onto silica gel and purified by flash chromatography (0-30% ethyl acetate/hexanes gradient). The fractions were concentrated. The crude material was purified by reverse phase HPLC. The fractions were lyophilized, redissolved in ethyl acetate and washed with saturated aqueous NaHCO$_3$. The organic layer was dried over anhydrous Na$_2$SO$_4$ and concentrated to afford the title compound (90 mg). LC/MS: Calc. C$_{21}$H$_{19}$N$_3$O$_2$S$_2$ 409.09 amu; Obs. [M+H]$^+$=410.1 amu.

Example IV

This example describes the synthesis of 4-(biphenyl-4-yl)-N-(2-chlorophenyl)thiazol-2-amine.

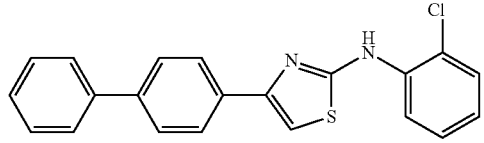

1-Biphenyl-4-yl-2-bromo-ethanone (69 mg, 0.25 mmol) was dissolved in acetone (1 mL) and the resulting solution added to a slurry of MgSO$_4$ (anhydrous, 60 mg) and (2-chloro-phenyl)thiourea (47 mg, 0.25 mmol) in acetone (2 mL). The reaction mixture was stirred at 60° C. for 30 h before brine (10 mL) and 28-30% aqueous NH$_3$ (2 mL) were added. The mixture was extracted with dichloromethane (2×10 mL) and the combined dichloromethane extracts washed with brine (10 mL). The organic solution was evaporated to dryness in vacuo and the residue obtained purified by reverse phase HPLC to provide the title compound (53 mg). LC/MS: Calc. C$_{21}$H$_{15}$ClN$_2$S 362.06 amu; Obs. [M+H]$^+$=363.1 amu.

Example V

This example describes the synthesis of N-(4-(2,4-dimethoxyphenyl)thiazol-2-yl)benzamide.

4-(2,4-Dimethoxyphenyl)thiazol-2-yl amine (100 mg, 0.423 mmol) was dissolved in dichloromethane (1.4 mL) and DIEA (147 μL, 0.846 mmol). Next, benzoyl chloride (59 μL, 0.50 mmol) was added to the reaction mixture and stirred at room temperature overnight. After this period, the reaction mixture was concentrated to dryness and redissolved in dichloromethane. The organic solution was washed with saturated aqueous NaHCO$_3$ and brine, respectively. The organic layer was dried over anhydrous Na$_2$SO$_4$, concentrated onto silica gel and purified by flash chromatography (0-50% ethyl acetate/hexanes gradient). The product was then purified by reverse phase HPLC to afford the title compound (27 mg). LC/MS: Calc. C$_{18}$H$_{16}$N$_2$O$_3$S 340.08 amu; Obs. [M+H]$^+$=340.7 amu.

Example VI

This example describes the synthesis of 4-(8H-indeno[1,2-d]thiazol-2-ylamino)phenol.

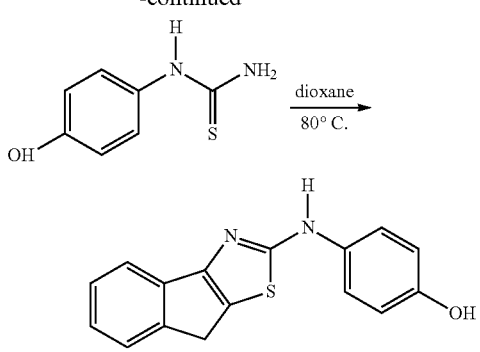

2-Bromo-1-indanone (200 mg, 0.948 mmol) and 1-(4-hydroxyphenyl)-2-thiourea (145 mg, 0.862 mmol) were placed in a microwave vial and suspended in dioxane (4 mL). The reaction vessel was sealed, placed in a microwave oven and heated at 80° C. for 1 hour. After this period, the reaction mixture was concentrated to dryness and redissolved in ethyl acetate, washed with saturated aqueous NaHCO$_3$ and brine, respectively. The organic layer was dried over anhydrous Na$_2$SO$_4$ and concentrated onto silica gel. It was then purified by flash chromatography (0-50% ethyl acetate/hexanes gradient) and HPLC to afford the title compound (55 mg). LC/MS: Calc. C$_{16}$H$_{12}$N$_2$OS 280.06 amu; Obs. [M+H]$^+$= 281.1 amu.

Example VII

This example describes the synthesis of 2-oxo-3-(2-(pyridin-2-yl)ethyl)-N-((tetrahydrofuran-2-yl)methyl)-1,2,3,4-tetrahydroquinazoline carboxamide.

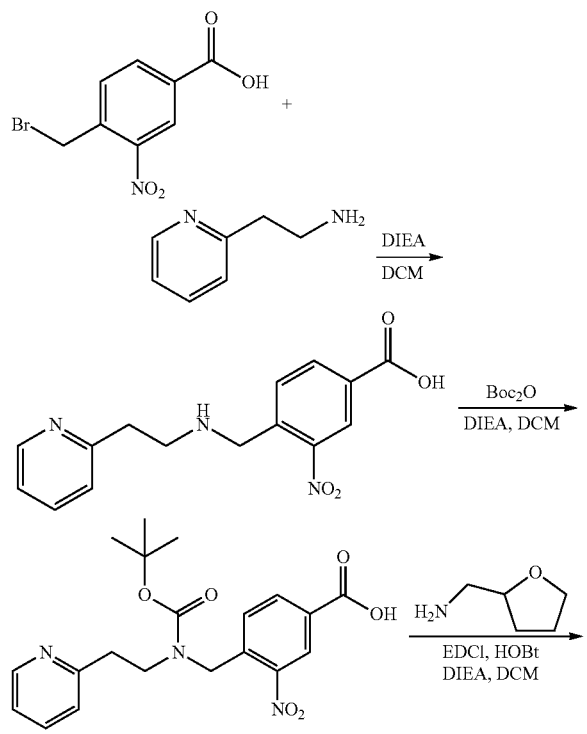

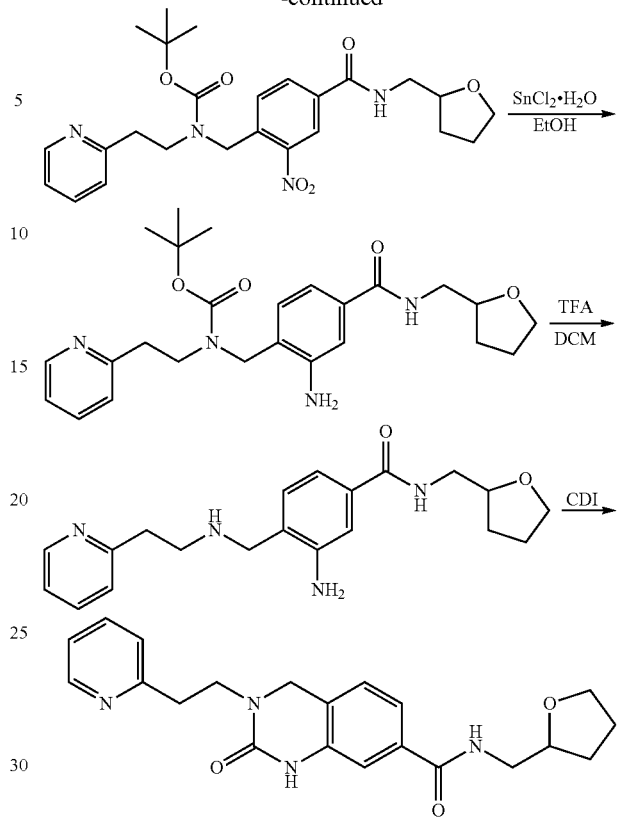

A solution of 4-Bromomethyl-3-nitrobenzoic acid (200 mg, 0.769 mmol) and 2-(2-aminoethyl) pyridine (104 mg, 0.846 mmol) in dichloromethane (2.5 mL) was treated with DIEA (268 μL). The resulting reaction mixture was heated at 50° C. for 1 hour. After this period, the mixture was concentrated in vacuo and the crude residue used in the next step without purification. LC/MS: Calc. C$_{15}$H$_{15}$N$_3$O$_4$ 301.10 amu; Obs. [M+H]$^+$=302.2 amu.

3-Nitro-4-((2-pyridin-2-yl-ethylamino)methyl)benzoic acid, compound obtained above, (231 mg, 0.769 mmol) and di-tert-butyl dicarbonate (201 mg, 0.922 mmol) were dissolved in dichloromethane (2.5 mL) and DIEA (268 1.53 mmol). The reaction mixture was heated at 50° C. for 1 hour. After this period, the reaction mixture was concentrated in vacuo and the residue used in the next step without purification. LC/MS: Calc. C$_{20}$H$_{23}$N$_3$O$_6$ 401.15 amu; Obs. [M+H]$^+$ = 402.6 amu.

A solution of 4-((tert-Butoxycarbonyl-(2-pyridin-2-yl)ethyl)amino)methyl)-3-nitro-benzoic acid (308 mg, 0.769 mmol), EDCI (179 mg, 1.15 mmol), HOBT (177 mg, 1.15 mmol) and DIEA (268 μL, 1.53 mmol) in dichloromethane (2.5 mL) was stirred at room temperature for 15 minutes. Next, tetrahydrofurfurylamine (96 μL, 0.92 mmol) was added to the reaction vessel and the reaction heated at 50° C. overnight. After this period, the reaction mixture was concentrated to dryness, redissolved in dichloromethane and washed with aqueous 1 M HCl and brine. The organic layer was dried over anhydrous Na$_2$SO$_4$, concentrated onto silica gel and purified by flash chromatography (0-100% ethyl acetate/hexanes gradient) to afford the desired material, tert-butyl 2-nitro-4-((tetrahydrofuran-2-yl)methylcarbamoyl)benzyl(2-(pyridin-2-yl)ethyl)carbamate (238 mg). LC/MS: C$_{25}$H$_{32}$N$_4$O$_6$ 484.23 amu; Obs. [M+H]$^+$=485.5 amu.

tert-Butyl 2-nitro-4-(((tetrahydrofuran-2-yl)methylcarbamoyl)benzyl(2-(pyridin-2-yl)ethyl)carbamate, from above, (238 mg, 0.492 mmol) and SnCl$_2$.2H$_2$O (279 mg, 1.23 mmol) were suspended in ethanol (1.6 mL) and stirred at 50° C. for 1 hour. The reaction mixture was concentrated to dryness, re-suspended in ethyl acetate, washed with water and brine, dried over anhydrous Na$_2$SO$_4$, concentrated onto silica gel and purified by flash chromatography (20 methanol:1 triethylamine:79 dichloromethane isocratic) to afford the desired intermediate, tert-butyl 2-amino-4-((tetrahydrofuran-2-yl)methylcarbamoyl)benzyl(2-(pyridin-2-yl)ethyl)carbamate (103 mg). LC/MS: Calc. C$_{25}$H$_{34}$N$_4$O$_4$ 454.25 amu; Obs. [M+H]$^+$=455.5 amu.

A solution of tert-butyl 2-amino-4-((tetrahydrofuran-2-yl)methylcarbamoyl)benzyl(2-(pyridin-2-yl)ethyl)carbamate (103 mg, 0.226 mmol) in dichloromethane (2 mL) was treated with TFA (2 mL). The reaction mixture was stirred at room temperature overnight. The reaction mixture was concentrated in vacuo, redissolved in dichloromethane and the mixture concentrated again. This was repeated twice and the crude material was taken to the next step without further purification. LC/MS: Calc. C$_{20}$H$_{26}$N$_4$O$_2$ 354.20 amu; Obs. [M+H]$^+$=355.4 amu 3-Amino-4-((2-(pyridin-2-yl)ethylamino)methyl)-N-((tetrahydrofuran-2-yl)methyl)benzamide, obtained above, (80 mg, 0.22 mmol) was dissolved in dichloromethane (1 mL) and DIEA (158 µL) and the resulting solution was allowed to stir at room temperature for 5 minutes. Next, CDI (44 mg, 0.27 mmol) was added to the reaction vessel and the mixture was allowed to stir at room temperature for 1 hour. Next, the reaction mixture was concentrated onto silica gel, and purified by flash chromatography (0-100% ethyl acetate/hexanes gradient) and reverse phase HPLC to afford the title compound (10 mg). LC/MS: C$_{21}$H$_{24}$N$_4$O$_3$ 380.18; Calc. amu; Obs. [M+H]$^+$=381.3 amu.

Example VIII

This example describes the synthesis of 2-(5-methoxy-1H-indol-3-yl)-N-((3-(naphthalen-2-yl)-1,2,4-oxadiazol-5-yl)methyl)ethanamine.

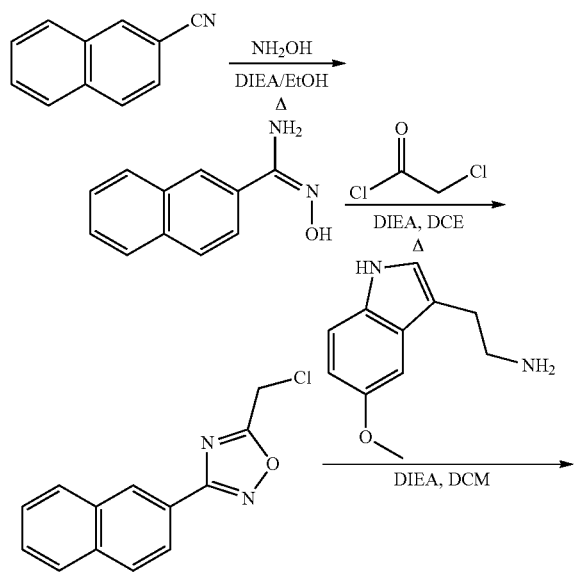

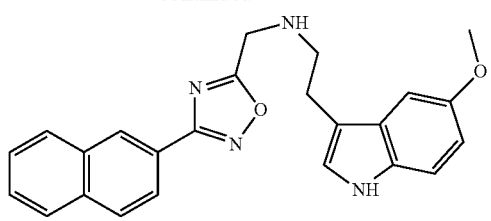

A solution of Naphthalene-2-nitrile (300 mg, 1.95 mmol) and hydroxylamine hydrochloride (164 mg, 2.35 mmol) in ethanol (6 mL) was treated with DIEA (683 3.91 mmol). The reaction mixture was heated at 50° C. overnight before it was concentrated and the crude product, N-hydroxy-naphthalene-2-carboxamidine, was used in the next step without further purification.

A solution of N-Hydroxy-naphthalene-2-carboxamidine (364 mg, 1.95 mmol) in dichloroethane (6 mL) and DIEA (683 µL, 3.91 mmol) was treated with a solution of chloroacetyl chloride (157 µL, 2.350 mmol) in dichloroethane (2 mL) which was added dropwise to the reaction vessel at room temperature. After the addition, the reaction mixture was heated at 50° C. for 4 hours. The reaction mixture was then concentrated to dryness and redissolved in dichloromethane. The organic layer was washed with saturated aqueous NaHCO$_3$ and brine, respectively. The organic layer was dried over anhydrous Na$_2$SO$_4$, concentrated onto silica gel and purified by flash chromatography (0-50% ethyl acetate/hexanes gradient) to afford the required intermediate, 5-chloromethyl-3-naphthalen-2-yl-[1,2,4]oxadiazole (102 mg).

A solution of 5-Chloromethyl-3-naphthalen-2-yl-[1,2,4]oxadiazole (100 mg, 0.408 mmol) in dichloromethane (1 mL) and DIEA (143 µL, 0.817 mmol) was treated with 5-methoxytryptamine (93 mg, 0.49 mmol). The reaction mixture was stirred at 50° C. overnight. The mixture was then concentrated to dryness in vacuo and redissolved in dichloromethane. The organic layer was washed with saturated aqueous NaHCO$_3$ and brine, dried over anhydrous Na$_2$SO$_4$, concentrated onto silica gel and purified by flash chromatography (0-50% ethyl acetate/hexanes gradient) to afford the title compound (94 mg). LC/MS: Calc. C$_{24}$H$_{22}$N$_4$O$_2$ 398.17 amu; Obs. [M+H]$^+$=399.2 amu.

Example IX

This example describes the synthesis of N$^2$-(2-(diethylamino)ethyl)-N$^2$-ethyl-N$^1$-(4-fluorobenzyl)-1-phenylethane-1,2-diamine.

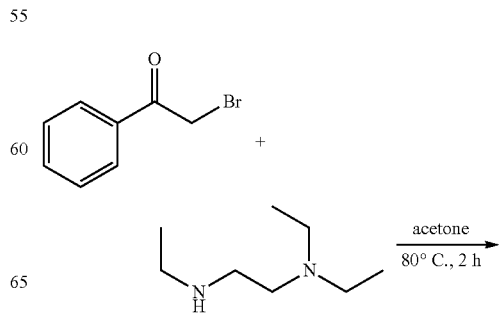

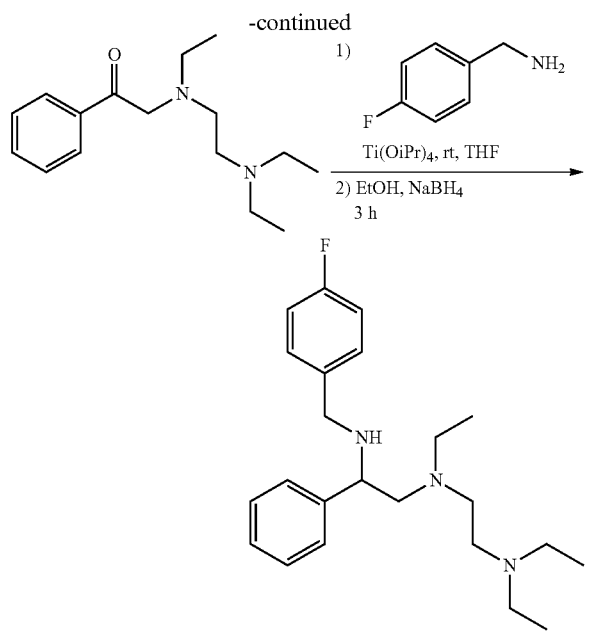

A solution of 2-bromoacetophenone (1.00 g, 5.02 mmol) and N,N,N'-triethyl-ethane-1,2-diamine (0.978 g, 6.03 mmol) in acetone (8 mL) was heated at 80° C. for 2 h. The solution was concentrated under vacuum and the residue obtained partitioned between dichloromethane (16 mL) and saturated aqueous NaHCO₃ solution (8 mL). The biphasic mixture was stirred at room temperature for 0.5 h and then the organic phase separated. The dichloromethane solution obtained above was treated with a solution of succinic anhydride (120 mg, 1.2 mmol) in dichloromethane (4 mL). The resulting reaction mixture was stirred at room temperature for 20 h. A solution of saturated aqueous NaHCO₃ (8 mL) was then added and the biphasic mixture was stirred at room temperature for 1 h. The organic layer was separated and the dichloromethane solution evaporated under reduced pressure. The brown oil obtained (1.13 g) was used in the next step without further purification.

The oil obtained above (210 mg, 0.8 mmol) and 4-fluorobenzylamine (95 mg, 0.087 mL, 0.76 mmol) were dissolved in THF (1 mL) and Ti(O$^i$Pr)₄ (450 mg, 0.49 mL, 1.6 mmol) then added. The resulting mixture was stirred at room temperature under a nitrogen atmosphere for 23 h before ethanol (1 mL) was added. Sodium borohydride (45 mg, 1.2 mmol) was then added in portions over 5 min Note: This is an exothermic reaction with gas evolution. The mixture was stirred for 3 h before 28-30% aqueous NH₃ (2 mL) was added. A tan precipitate formed and the slurry was stirred for 0.5 h before the precipitate was removed by filtration, washed with THF (3×2 mL), and the combined filtrates were concentrated under reduced pressure. The residue was partitioned between dichloromethane (5 mL) and water (5 mL), the phases separated and the aqueous phase extracted with dichloromethane (3 mL). The combined dichloromethane extracts were evaporated under reduced pressure to provide an orange-brown oil (264 mg). The product was isolated by preparative reverse phase HPLC to yield the title compound (54 mg). LC/MS: Calc. $C_{23}H_{34}FN_3$ 371.27 amu; Obs. [M+H]⁺ =372.3.

Example X

Figure 3:
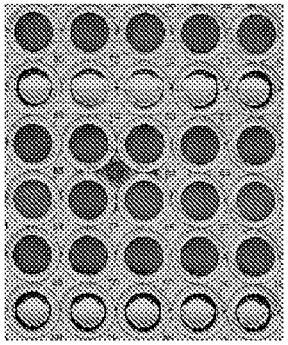
FIG. 3 shows microtiter plate analysis of human HSF1 activation. Yeast hsfΔ cells harboring the GAL1-yeast HSF (yHSF) plasmid. On galactose (gal) all cells were viable due to galactose-inducible expression of yHSF. On glucose (glu) expression of yHSF was extinguished and cells were inviable when they express wild type human HSF1 or the empty vector. However, yhsfΔ cells expressing a constitutively trimerized human HSF1 protein (HSF11z4m) were viable in the absence of yeast HSF. All wells within a given row of the microtiter plate section contained the same yeast strain to show consistency. Plasmids transformed into the strain and carbon sources were indicated.
Figure 4:
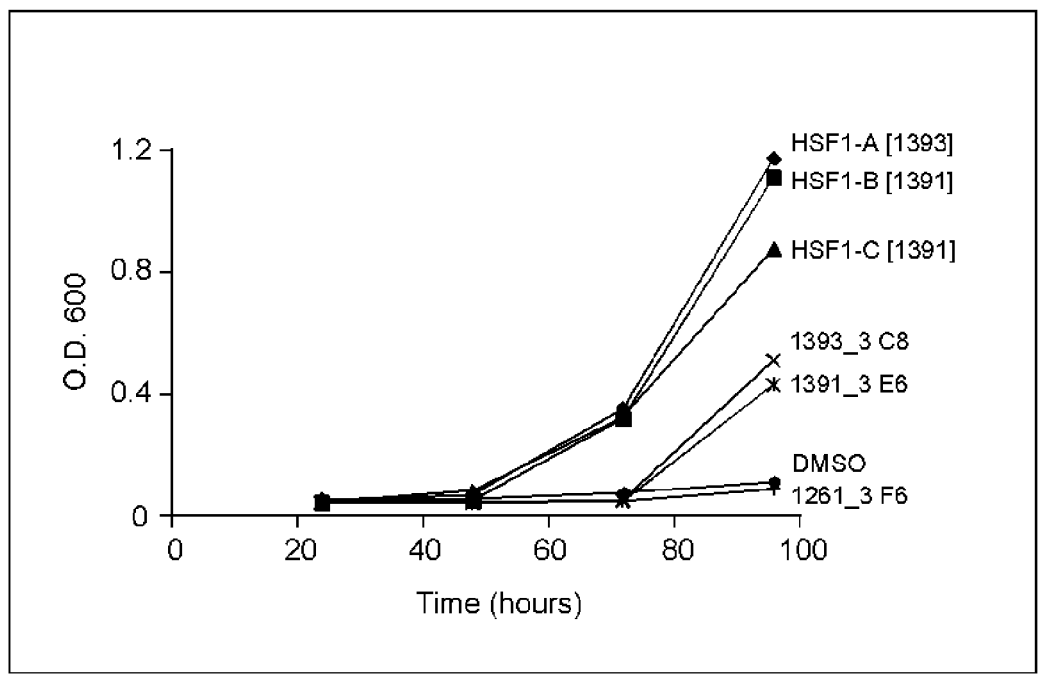
FIG. 4 show growth of the yhsfΔ: human HSF1 yeast strain in the presence of library compounds. Growth in the presence of solvent (1% DMSO) or 10 micromolar concentrations of the compounds (labeled) is shown as a function of time versus optical density at 600 nm.

This example describes the optimization of growth conditions for the DTY512 strain. As demonstrated in FIG. 3, the growth conditions for a yhsfΔ strain harboring 1) a yeast HSF gene coupled with a GAL promoter and 2) a pRS424-GPD-hHSF1 plasmid for hHSF1 expression (the DTY512 strain) were optimized from petri dishes to 96 well microtiter dish format. Cells were grown in Synthetic Complete medium lacking uracil and tryptophan to select for plasmid maintenance, in the presence of the non-inducing/non-repressing carbon source raffinose (2%). Galactose concentrations (0.01%) were empirically identified that induce sufficient levels of yeast HSF for robust yeast cell viability, while rendering cells sensitive to strong glucose repression of yeast HSF expression after the addition of 4% glucose. The screen cells are grown to midlog phase in selective synthetic complete medium with 2% raffinose and 0.01% galactose. The culture was then diluted to ~5,000 cells/ml in the same growth medium in which 4% glucose was substituted for the galactose, to initiate glucose repression of yeast HSF expression. Cells (200 microliters) were seeded into 96 well microtiter dishes at ~1,000 cells/well and compound or carrier solvent (dimethylsulfoxide, DMSO) distributed independently to each well using a Beckman Biomek FX liquid handling robot under sterile conditions. Plates were incubated at 30° C. and optical density measured over time using an attached SpectraMax Plus Plate Reader. Yeast culture growth curves were generated for each microtiter well and slopes calculated over the course of 96 hours. As shown in FIG. 4, the growth of cells was quantitatively followed in each microtiter well, the background growth of cells expressing wild type human HSF1 with either no addition or DMSO alone is very low and allowed for facile qualitative detection of positive candidates in the screen.

Example 11

This example describes validation of candidate HSF1 activating compounds. As shown in FIG. 3 appropriate growth conditions, galactose induction and glucose repression parameters for application of the yeast-based human HSF1 activator screen to a high throughput 96-well format was identified. FIG. 4 show a sample of compounds taught herein (see structures below) that stimulated yeast cell growth with different efficacy, with the DMSO solvent as a control.

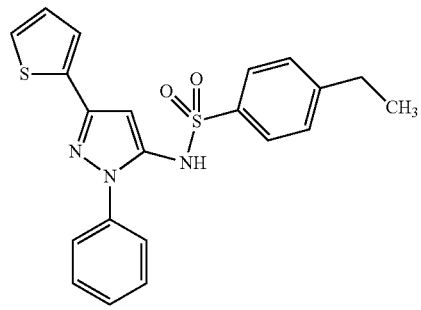

HSF1-A

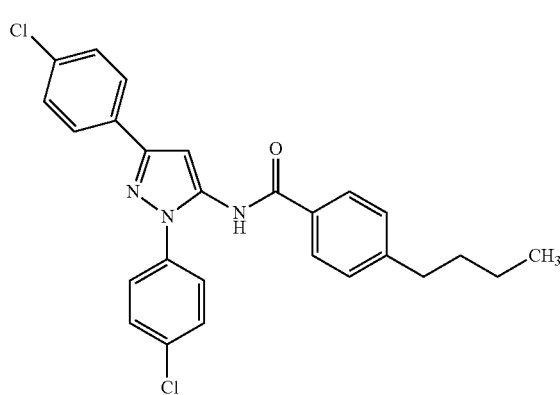

HSF1-B

HSF1-C

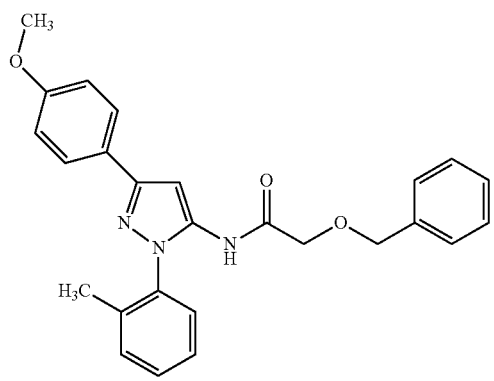

1393-3 C8

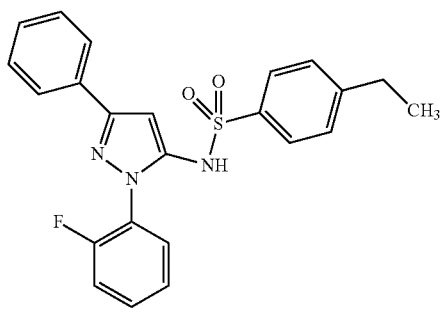

1391-3 E6

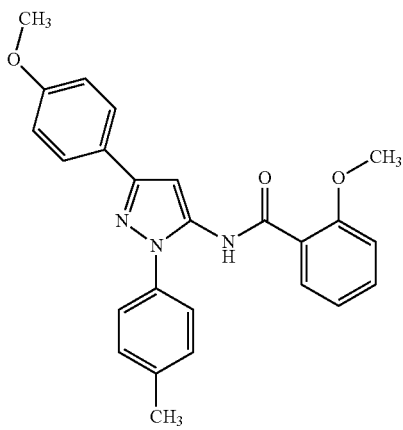

1261-3 F6

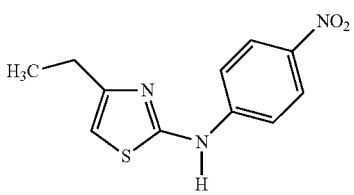

All publications and patents mentioned in the above specification are herein incorporated by reference for all purposes. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

```
                             SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

We claim:
1. A compound selected from the group consisting of:
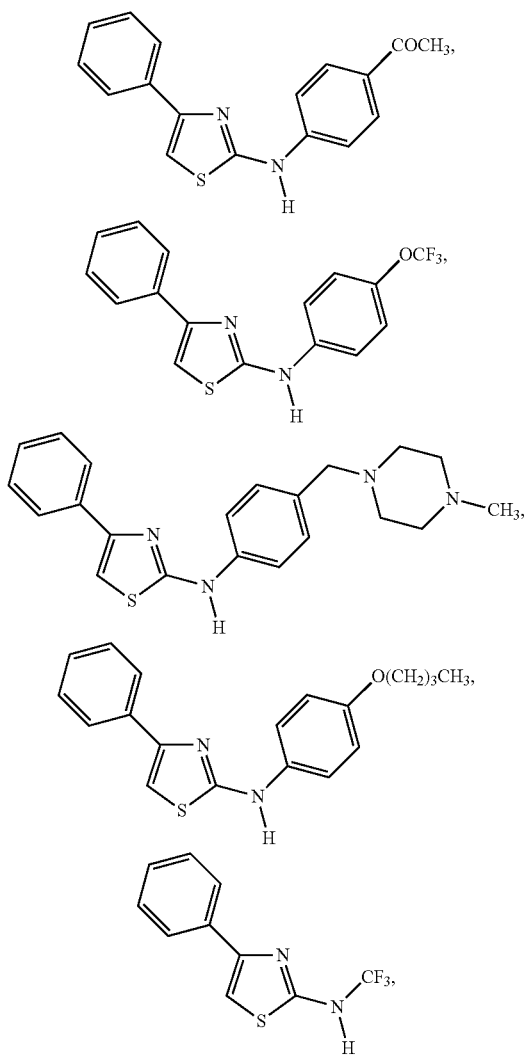
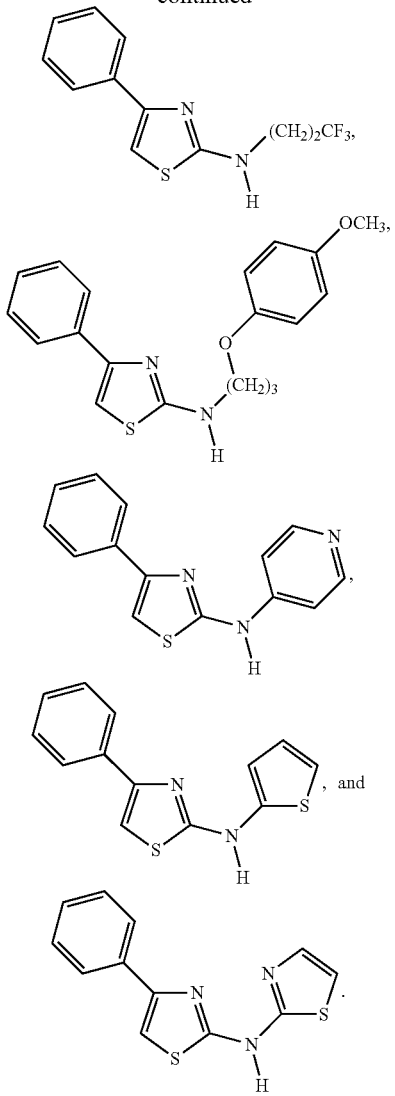

<400> SEQUENCE: 1
ngaannttcn ngaan                                                      15
```